United States Patent
Lu et al.

(10) Patent No.: US 11,287,404 B2
(45) Date of Patent: Mar. 29, 2022

(54) ANALYSIS APPARATUS WITH SPECTROMETER

(71) Applicant: International Business Machines Corporation, Armonk, NY (US)

(72) Inventors: Minhua Lu, Mohegan Lake, NY (US); Vince Siu, Thornhill (CA); Russell Budd, North Salem, NY (US); Evan Colgan, Montvale, NJ (US)

(73) Assignee: International Business Machines Corporation, Armonk, NY (US)

( * ) Notice: Subject to any disclaimer, the term of this patent is extended or adjusted under 35 U.S.C. 154(b) by 202 days.

(21) Appl. No.: 15/851,244

(22) Filed: Dec. 21, 2017

(65) Prior Publication Data

US 2019/0195844 A1   Jun. 27, 2019

(51) Int. Cl.
*G01N 31/22* (2006.01)
*G01N 33/543* (2006.01)
(Continued)

(52) U.S. Cl.
CPC ........... *G01N 31/22* (2013.01); *B01F 31/651* (2022.01); *B01F 33/30* (2022.01); *B01L 3/5027* (2013.01); *B01L 3/502738* (2013.01); *G01N 21/00* (2013.01); *G01N 33/54366* (2013.01); *B01L 2200/16* (2013.01); *B01L 2300/0654* (2013.01);
(Continued)

(58) Field of Classification Search
CPC .. G01N 31/22; G01N 33/54366; G01N 21/00; G01N 21/255; B01F 13/0059; B01F 11/0074; B01L 3/502738; B01L 2200/16; B01L 2300/0654; B01L 2300/0816; B01L 2300/0864; B01L 2300/087; B01L 2400/0406; B01L 3/5027
See application file for complete search history.

(56) References Cited

U.S. PATENT DOCUMENTS

| | | |
|---|---|---|
| 3,443,903 A | 5/1969 | Haack et al. |
| 5,334,348 A | 8/1994 | Saito et al. |

(Continued)

FOREIGN PATENT DOCUMENTS

| | | |
|---|---|---|
| WO | WO2016148646 A1 | 9/2016 |
| WO | WO2017021971 A1 | 2/2017 |

*Primary Examiner* — Samuel P Siefke
*Assistant Examiner* — Quocan B Vo
(74) *Attorney, Agent, or Firm* — Kristofer Haggerty; Michael J. Chang, LLC

(57) ABSTRACT

An apparatus having a spectrometer and techniques for use thereof for efficient and effective point-of-care diagnostics are provided. In one aspect, a device is provided. The device includes: an intake port; fluidic channels connecting the intake port to a detecting chamber(s), wherein the detecting chamber(s) is configured to permit optical measurements of a fluid sample; a vent leading away from the detecting chamber(s); and a liquid blocker between the detecting chamber(s) and an opening of the vent, wherein the liquid blocker permits air to pass therethrough while at the same time restricting liquid flow. A method for analyzing a fluid sample is also provided. The method includes: introducing the fluid sample to the device; contacting the fluid sample with a reagent(s) prior to the fluid sample entering the detecting chamber(s); and making optical measurements of the fluid sample in the detecting chamber(s).

14 Claims, 16 Drawing Sheets

(51) Int. Cl.
B01L 3/00 (2006.01)
G01N 21/00 (2006.01)
B01F 31/65 (2022.01)
B01F 33/30 (2022.01)
G01N 21/25 (2006.01)

(52) U.S. Cl.
CPC . *B01L 2300/087* (2013.01); *B01L 2300/0816* (2013.01); *B01L 2300/0864* (2013.01); *B01L 2400/0406* (2013.01); *G01N 21/255* (2013.01)

(56) References Cited

U.S. PATENT DOCUMENTS

| | | | | |
|---|---|---|---|---|
| 5,599,503 | A * | 2/1997 | Manz | B01L 3/502715 204/452 |
| 5,726,751 | A * | 3/1998 | Altendorf | B01L 3/502715 356/246 |
| 6,277,646 | B1 | 8/2001 | Guirguis et al. | |
| 7,758,815 | B2 | 7/2010 | Hartselle | |
| 9,056,291 | B2 | 6/2015 | Battrell et al. | |
| 9,597,010 | B2 | 3/2017 | Thompson et al. | |
| 2002/0009390 | A1 | 1/2002 | Lappe et al. | |
| 2002/0058273 | A1* | 5/2002 | Shipwash | G01N 33/6812 435/6.12 |
| 2003/0092034 | A1* | 5/2003 | Cooper | B01L 3/5085 435/6.19 |
| 2003/0219196 | A1* | 11/2003 | Weng | G01N 21/6452 506/32 |
| 2004/0189311 | A1* | 9/2004 | Glezer | B01L 3/502715 324/444 |
| 2005/0129580 | A1* | 6/2005 | Swinehart | B82Y 30/00 422/400 |
| 2005/0136545 | A1* | 6/2005 | Schmid | B01L 3/50273 436/45 |
| 2005/0136685 | A1* | 6/2005 | Takenaka | B01L 3/502723 438/778 |
| 2007/0099290 | A1* | 5/2007 | Iida | B01L 3/502738 435/287.2 |
| 2007/0281322 | A1* | 12/2007 | Jaffe | G01J 3/10 435/7.1 |
| 2008/0070311 | A1* | 3/2008 | Li | G01N 15/1459 436/63 |
| 2008/0173817 | A1* | 7/2008 | Goldstein | G01N 21/783 250/338.1 |
| 2009/0165876 | A1* | 7/2009 | Atkin | F16K 99/0057 137/825 |
| 2010/0261223 | A1* | 10/2010 | Margraf | B01L 3/502753 435/29 |
| 2011/0044369 | A1* | 2/2011 | Andry | G02B 6/4204 372/50.124 |
| 2011/0223673 | A1 | 9/2011 | Profitt | |
| 2012/0238032 | A1* | 9/2012 | Durniak | G01N 15/1436 436/164 |
| 2013/0030366 | A1 | 1/2013 | Robertson et al. | |
| 2013/0130262 | A1* | 5/2013 | Battrell | B01L 3/50273 435/6.12 |
| 2014/0011266 | A1* | 1/2014 | Webster | B01L 7/52 435/286.1 |
| 2014/0080118 | A1* | 3/2014 | Bates | G01N 33/54333 435/5 |
| 2014/0178861 | A1* | 6/2014 | Duer | G01N 33/54373 435/5 |
| 2014/0268120 | A1* | 9/2014 | Assefa | G01N 21/00 356/237.5 |
| 2015/0024426 | A1* | 1/2015 | De Oliveira Garcia Da Fonseca | G01N 15/05 435/29 |
| 2015/0185159 | A1* | 7/2015 | Morita | G06K 9/00134 422/82.05 |
| 2015/0248833 | A1 | 9/2015 | Arne et al. | |
| 2016/0223456 | A1* | 8/2016 | Urey | G01N 29/022 |
| 2016/0279632 | A1* | 9/2016 | Delamarche | B01L 3/50273 |
| 2017/0205351 | A1* | 7/2017 | Astier | G01N 21/6428 |
| 2017/0350821 | A1* | 12/2017 | Delamarche | B01L 3/5023 |
| 2018/0080060 | A1* | 3/2018 | Gifford | G01N 15/1056 |

\* cited by examiner

| Target Analyte | Reagent | Time of Incubation |
|---|---|---|
| Specific Gravity | Bromothymol Blue | |
| pH (4.6 – 8.0) | Methyl Red/Bromothymol Blue | 60 seconds |
| Protein | Tetrabromothymol Blue | 60 seconds |
| Glucose | Glucose oxidase Peroxidase Potassium Iodide | 30 seconds |
| Ketones | Sodium Niroprusside | 40 seconds |
| Blood | Diisopropylbenzene Dihydroperoxide tetramethylbenzidine | 60 seconds |
| Bilirubin | 2,4-Dichloroanaline diazonium salt | 30 seconds |
| Urobilirubin | p-Dimethylaminobenzaldehyde | 60 seconds |
| Nitrite | p-Arsanilic acid 1,2,3,4-Tetrahydro-benzo (h) quinoline-3-ol | 60 seconds |
| Leukocyte Esterase | Pyrrole amino acid ester Diazonium salt | 2 minutes |

FIG. 19

ANALYSIS APPARATUS WITH SPECTROMETER

FIELD OF THE INVENTION

The present invention relates to optical analysis of fluid samples, and more particularly, to an analysis apparatus having a spectrometer and techniques for use thereof for efficient and effective point-of-care diagnostics.

BACKGROUND OF THE INVENTION

Diagnostics play a critical role for the detection and prevention of diseases or health-related conditions and for the follow-up or daily care of chronic diseases. Diagnostic tools are used for instance to detect proteins, hormones, pathogens, toxins or metabolites for patients suffering from chronic cardiac diseases, diabetes, infections or allergies, just to name a few. However, the amount of reliable and accurate point-of-care diagnostics available to patients for home therapy or to medical personnel in remote locations is somewhat limited, with most of the more complicated tests being performed using more sophisticated techniques/equipment in clinical labs.

For instance, a common diagnostic tool is a test strip. Test strips are typically formed from a porous material that, via capillary action, transport a liquid sample across the strip. As the sample moves across the strip it contacts one or more areas containing reagents that react with the sample (or absent a target analyte do not react) forming a complex. Accumulation of the complexes changes a color of the strip. The test strip must then be read using a benchtop analyzer and/or other diagnostic tool capable of extracting data from the strip.

Typically, a sample is collected at one location (e.g., a patient sample collected by a doctor or clinician at a hospital), stored (e.g., at the hospital awaiting shipment and/or at one or more various other locations during transport), and then transported to a lab where the sample is tested (e.g., using a test strip) and data is extracted from the sample (e.g., by analyzing the test strip). Thus, a lot of handling and elapsed time is involved with the rather straightforward analysis of the sample.

Any mishandling (e.g., temperature excursions, exposure to light or other ultraviolet (UV) radiation, etc.) can degrade the sample, as can the simple passage of time. The best evaluation would be of a sample made at the time of collection.

Alternatively, test strips can be used and then read by eye, for example, by comparison with a chart comparing colors with certain results. This technique is however extremely subjective and thus can lead to faulty readings. For instance, the color displayed on the test strip might be in between two different data points on the chart, and it is then up to the user to make a judgment call about the reading.

Thus, improved point-of-care diagnostics would be desirable.

SUMMARY OF THE INVENTION

The present invention provides an apparatus having a spectrometer and techniques for use thereof for efficient and effective point-of-care diagnostics. In one aspect of the invention, a device is provided. The device includes: an intake port; fluidic channels connecting the intake port to at least one detecting chamber, wherein the at least one detecting chamber is configured to permit optical measurements of a fluid sample in the at least one detecting chamber; a vent leading away from the at least one detecting chamber; and a liquid blocker between the at least one detecting chamber and an opening of the vent, wherein the liquid blocker permits air to pass therethrough while at the same time restricting liquid flow.

In another aspect of the invention, a method is provided. The method includes: introducing a fluid sample to a device having an intake port, fluidic channels connecting the intake port to at least one detecting chamber, a vent leading away from the at least one detecting chamber, and a liquid blocker between the at least one detecting chamber and an opening of the vent, wherein the liquid blocker permits air to pass therethrough while at the same time restricting liquid flow; contacting the fluid sample with at least one reagent prior to the fluid sample entering the at least one detecting chamber; and making optical measurements of the fluid sample in the at least one detecting chamber.

A more complete understanding of the present invention, as well as further features and advantages of the present invention, will be obtained by reference to the following detailed description and drawings.

BRIEF DESCRIPTION OF THE DRAWINGS

FIG. 19 is a diagram illustrating exemplary reagents and target analytes according to an embodiment of the present invention;

DETAILED DESCRIPTION OF PREFERRED EMBODIMENTS

Provided herein are diagnostic devices that can be coupled to, and read by a spectrometer, thereby enabling users to perform point-of-care diagnostics on samples when and where they are collected. Thus, any degradation of the sample due to mishandling or the simple passing of time between when samples are collected and when they are tested can be avoided altogether.

The term "spectrometer" as used herein refers generally to an apparatus for measuring of light spectrums. For instance, in some exemplary embodiments provided herein, the spectrometer includes at least one light source and at least one light detector configured to detect the light (from the light source) that has passed through the sample. In other embodiments, the spectrometer includes at least one light source in combination with at least one camera, wherein the camera is configured to capture images of the sample (illuminated by the light source) from which data can be extracted.

The present diagnostic devices and techniques for use thereof can be implemented in a variety of different applications from medical testing to biological and chemical testing, environmental analysis, etc. For instance, with medical diagnostics a sample collected from a patient can be tested at the point of collection, such as by the patient at home, by a doctor or nurse at the hospital, etc. By way of example only, urinalysis performed using the present techniques can test for a variety of different biomarkers such as pH, specific gravity, leucocytes, nitrate, protein, glucose, ketones, urobilinogen, bilirubin, and blood, and may also include other biomarkers for sepsis/inflammation, bacterial speciation, tumor markers, and fibril aggregation. The present diagnostic devices are also well suited for use by researchers in the field. For instance, a user collecting water samples can easily use the device to analyze the samples at the point of collection to detect chemicals, biologics, contaminants, etc.

Figure 1:
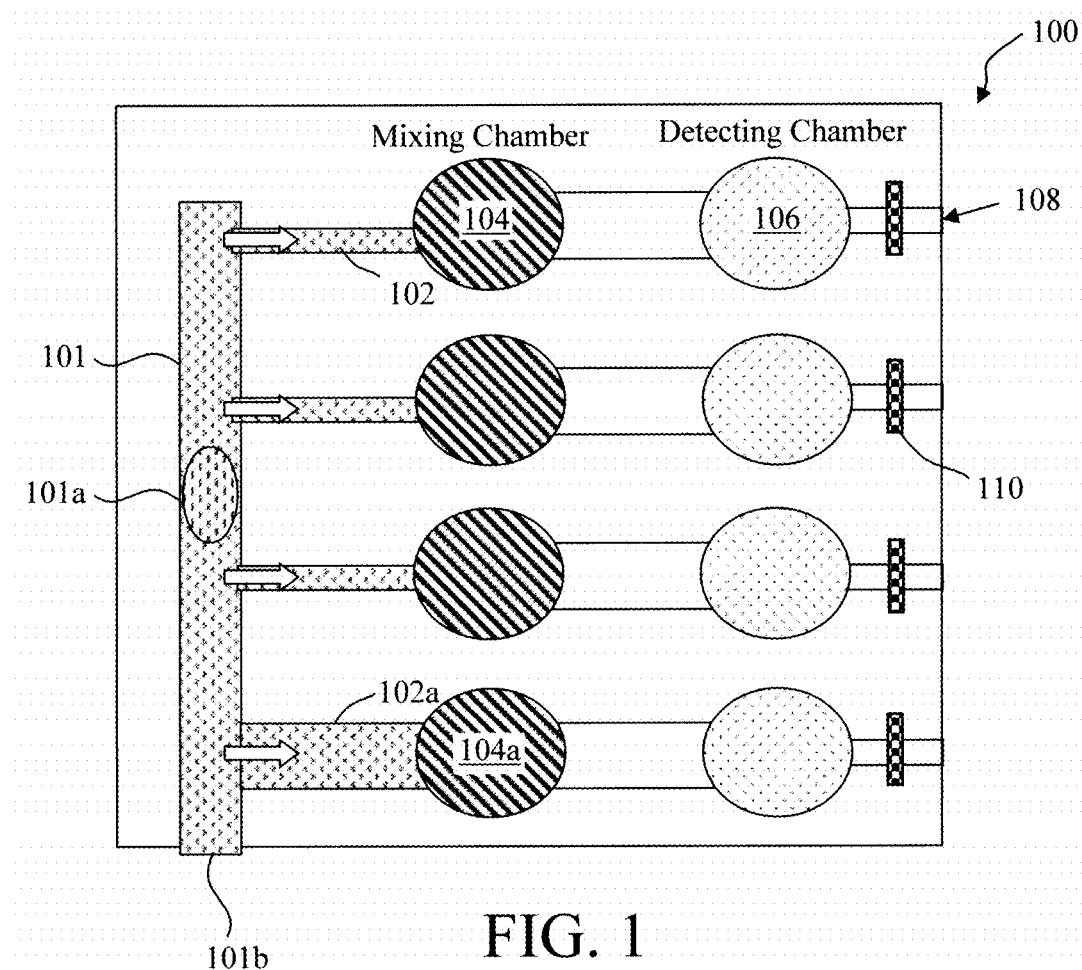
FIG. 1 is a top-down diagram of an exemplary diagnostic device according to an embodiment of the present invention.
Figure 2:
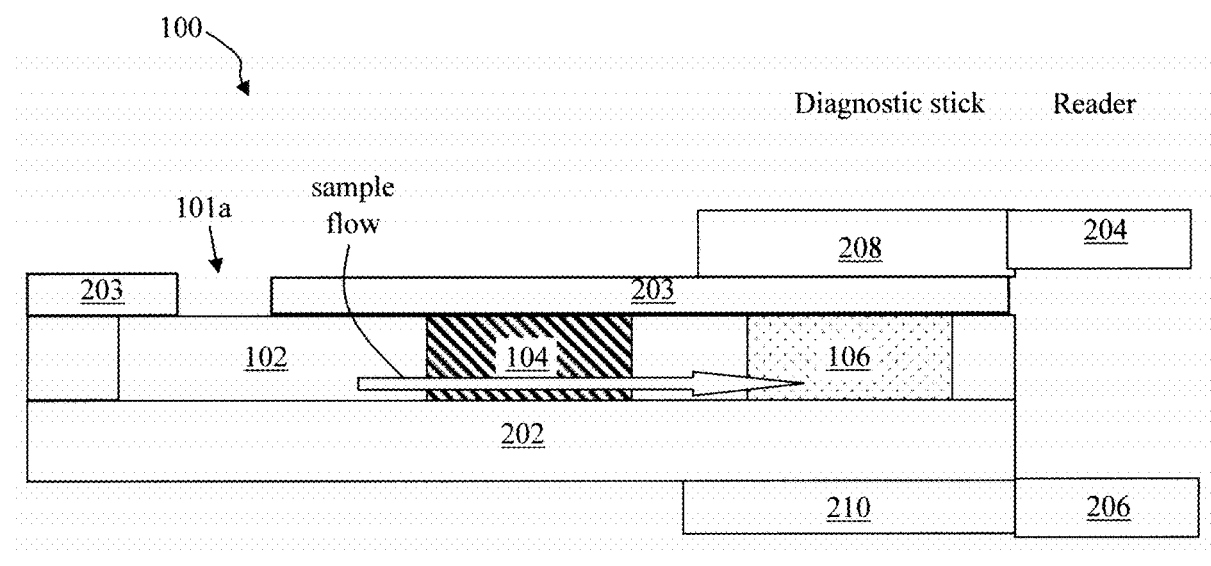
FIG. 2 is a side view diagram of the diagnostic device of FIG. 1 where waveguides are present on opposite sides of the detecting chambers according to an embodiment of the present invention.

A diagnostic device 100 according to a first exemplary embodiment is shown illustrated in FIG. 1 (top-down view) and FIG. 2 (side view). As shown in FIG. 1, device 100 includes a main sample transport region 101 at the entrance to multiple fluidic channels 102. As shown in FIG. 1, the main transport region 101 has sample intake ports 101a and 101b. The intake port 101a is an opening in a cover of the device (see below) and the intake port 101b enables access to region 101 from a side of the device.

The fluidic channels 102 connect the intake ports 101a,b to at least one mixing chamber 104 and at least one detecting chamber 106. Thus, the fluidic channels 102 deliver a fluid sample (dispensed via the intake ports 101a and/or 101b into region 101) to the at least one mixing chamber 104 and to at least one detecting chamber 106 by capillary force. It is notable that the use of separate mixing and detecting chambers is optional, and embodiments are considered herein where the mixing and detecting is conducted in a common (mixing/detecting) chamber.

In general, the fluid sample can be any liquid analyte. For instance, as provided above, the fluid sample can be a sample collected from a patient (e.g., for urinalysis), an environmental assay (e.g., for water testing), etc.

The mixing chambers 104 each contain at least one reagent that can react with components (also referred to herein as target analytes) that may be found in the sample. As shown in FIG. 1, the device 100 can include multiple mixing chambers 104. This is however not a requirement. For instance, if the device 100 is configured to detect the presence of a single target analyte, then a single mixing chamber can be present containing the respective reagent. To use a non-limiting illustrative example, say for example that researchers are interested in determining the presence (or absence) of a specific contaminant in drinking water samples. The reagent for the contaminant can be included in a single mixing chamber 104 which enables the researchers to easily and effectively know whether or not the contaminant is in the sample.

Multiple mixing chambers 104, however, provide a broader spectrum of data that can be extracted from the device 100. For instance, different reagents can be included in different mixing chambers 104 thus enabling testing against a panel of analytes. Further, different amounts of the reagents can be included in the mixing chambers 104. This can allow the reagent-to-analyte ratio to be optimized for a broader range of analyte concentrations and to enhance analyte detection.

According to an exemplary embodiment, the reagents are used with dyes that alter the color of the sample if and when the reagent interacts with the target analyte in the sample. To use a simple example to illustrate this concept, glucose oxidase is an enzyme commonly used as a reagent for the detection of glucose (as a target analyte). If present, glucose will bind with the glucose oxidase to form gluconic acid and hydrogen peroxide. The presence of hydrogen peroxide will interact with a second enzyme, peroxidase, to oxidize a chromogen (a dye) and change it from one color (or colorless dye) to another color (or color product). This color product will have a unique absorption profile with peak wavelengths that can be tracked over time. The intensity of the peak wavelength will correspond to the concentration of the analyte (i.e. glucose) present. Various chromogens for glucose detection exist and can include, but are not limited to, potassium iodide (KI), tetramethylbenzidine (TMB), 2,2'-azino-di-(3-ethyl-benzthiazoline-6-sulphonic acid) (ABTS), etc. Thus, if glucose oxidase and the respective chromogen (dye) are present in the mixing chambers 104 and the fluid sample passing through the mixing chambers 104 contains glucose, then the glucose oxidase will react with glucose and, via the dye, color/change a color of the sample that ends up in the detecting chambers 106 (see below). Alternatively, if the sample does not contain glucose, then no reaction occurs in the mixing chambers 104, and the color (or colorlessness) of the sample entering the detecting chambers will not be altered.

Further, as provided above, different amounts of the reagents can be included in the mixing chambers 104. By varying the amount of the reagent, the dye/reagent ratio can be tuned for better sensitivity and response to the analyte in a certain concentration. For example, a dye/reagent formulation that is sensitive to detect a low concentration of the target analyte may result in a saturated response for higher concentrations of analyte, while a formulation that is suitable to detect a high concentration of analyte might not be sensitive enough to detect low concentrations of the analyte.

To use an illustrative, non-limiting example, creatinine is an important biomarker found in serum and in urinalysis samples. Creatinine is a measure of how much muscle tissue is broken down, and is an early indicator for kidney disease and failure. By way of example only, a colorimetric approach with three enzymes can be used to detect creatinine in serum. The clinical range of creatinine in serum is roughly from about 0.3 milligrams per deciliter (mg/dL) to about 20 mg/dL, while in urinalysis samples the creatinine concentration ranges from about 10 mg/dL to about 300 mg/dL. There are different chemistries optimized for detection of creatinine in the 0.3-20 mg/dL and the 10-300 mg/dL range. If a specific sample has a creatinine concentration higher than the sensor with the lower sensitivity (i.e., 0.3-20 mg/dL), the signal may be saturated and the sample would need to be diverted to the sensor that can measure the higher concentration (i.e., 10-300 mg/dL). With the opposite case, i.e., if there is a very low concentration of creatinine in the sample, the sensor that can measure the lower concentration (i.e., 0.3-20 mg/dL) would be more ideal to make the measurement.

The fluidic channels 102 are (fluidly) connected to the mixing chambers 104. It is notable that the fluidic channels 102 are configured to deliver (see arrows) the sample to each of the mixing chambers 104. For instance, it is assumed that a single sample is being introduced into the device 100 via the intake ports 101a,b. The amount of sample delivered to the mixing chambers 104 is determined by the volume of the chamber.

Further, one or more of the fluidic channels 102 can be configured to be larger/smaller than the other fluidic channels 102 thereby regulating the flow rate of the sample to the corresponding mixing chamber 104 for a given sample size. See, for example, FIG. 1 where one of the fluidic channels 102a is larger than the other fluidic channels 102, and thereby the flow rate of the sample to the corresponding mixing chamber 104a is greater than to the other mixing chambers 104. As such, that mixing chamber 104a is filled faster than that other mixing chambers 104.

Referring back to FIG. 1, the mixing chambers 104 are in turn (fluidly) connected to at least one detecting chamber 106. See FIG. 1. The notion is that the fluid sample, when passing through the device 100, will first pass through the mixing chambers 104 where the sample mixes/reacts with the reagents. The sample then passes to the detecting chambers 106 where a spectrometer (coupled to the detecting chambers 106) takes readings.

A vent 108 leading away from each of the detecting chambers 106 removes air and allows the flow of fluid into the respective chambers. Liquid blockers 110 are inserted after the detecting chambers 106 before the opening of the vent 108 to restricts the flow of liquid out from the vent 108. The liquid blockers 110, however, permit air to pass through. The use of liquid blockers 110 is important for quantitative detection. It prevents sample overflow from washing away the reacted sample that might cause error in the concentration measurement. The liquid blockers 110 can be a porous material or membrane that is gas permeable but does not pass liquid or has a high flow resistance to liquid. By way of example only, suitable materials that pass air but do not readily pass liquid include, but are not limited to, Gor-Tex®, fine hydrophobic mesh, etc.

Figure 3:
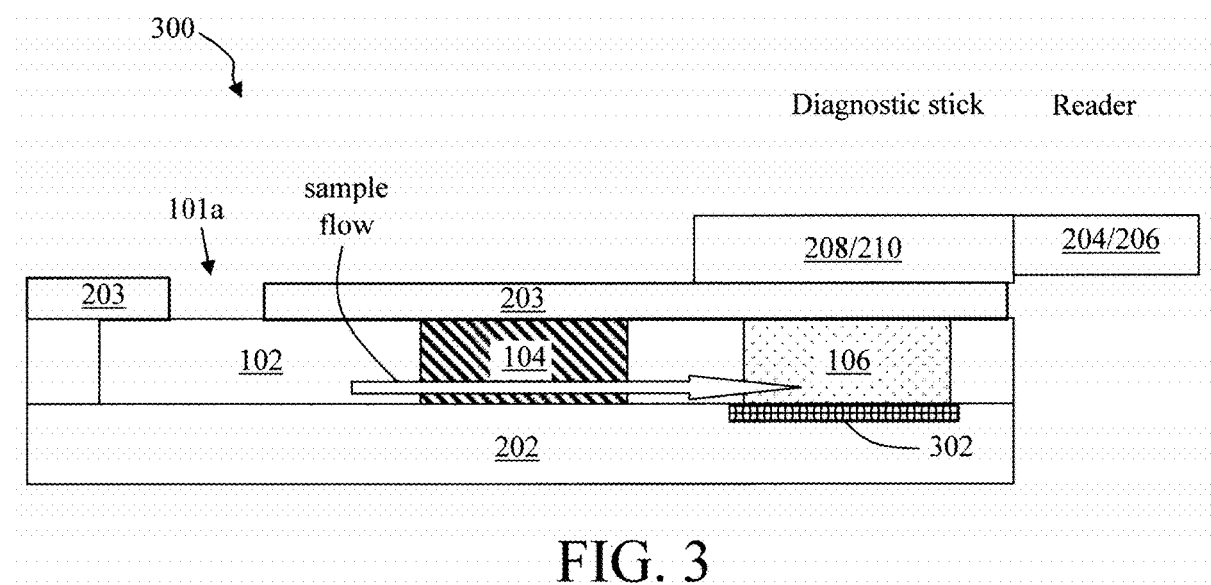
FIG. 3 is a side view diagram of the diagnostic device of FIG. 1 where the waveguides are present on a same side of the detecting chambers opposite a reflector according to an embodiment of the present invention.

Referring now to the side view of device 100 shown in FIG. 2, it can be seen that the intake port 101a, fluidic channels 102, the mixing chambers 104 and the detecting chambers 106 are oriented alongside one another on a substrate 202. According to an exemplary embodiment, the substrate is flexible. Further, as shown in FIG. 2, a cover 203 is present over, and sealing the fluidic channels 102, the mixing chambers 104 and the detecting chambers 106. According to one exemplary embodiment, optical readings are taken through the substrate 202 and cover 203. In that case, the substrate 202 and the cover 203 are both preferably transparent to light at the detecting chambers 106. Suitable transparent materials for substrate 202 and cover 203 include, but are not limited to, polyester, polyethylene Terephthalate (PET), polyethylene Naphthalate (PEN), glass, and/or polycarbonate. According to another exemplary embodiment, the substrate 202 is nontransparent and a reflector is used under the detection chambers 106 to reflect light. This alternative embodiment is described in conjunction with the description of FIG. 3, below.

As shown in FIG. 2, a sample passes through the mixing chambers 104 to the detecting chambers 106. Separate mixing and detecting chambers are desirable when, for example, more than one step of a reaction happens during the analysis and the detecting chambers 106 and/or the passages between the mixing chambers 104 and the detecting chambers 106 contain reagents for different steps of the reaction. Another application for separate mixing and detecting chambers is when a special process or storage condition is required for the reagent, and/or when a chamber with clear window or the waveguide lamination process is not suitable for the reagent. In those cases, separate mixing chambers can help maintain the viability of the reagents.

As shown in FIG. 2, a spectrometer ("Reader") component includes at least one light source 204 and at least one light detector 206 that are coupled to the detecting chambers 106 via waveguides 208 and 210, respectively. Waveguides 208 and 210 transmit and receive light from/to the light source 204 and the light detector 206, respectively. In the exemplary embodiment shown in FIG. 2, the waveguides 208 and 210 are located on opposite sides, e.g., above and below, the detecting chambers 106, respectively. However, embodiments are also contemplated herein where the waveguides are located on the same side of the detecting chambers 106, and reflective optical readings are made. See below. Suitable light sources include, but are not limited to, light emitting diodes (LEDs), a laser, a Xenon arc lamp, a halogen lamp, an incandescent lamp, etc., and suitable light detectors include, but are not limited to, photodiodes (PD), a charge-coupled device/complementary metal oxide semiconductor CCD/CMOS imager, a photo multiply tube, a wavelength-sensitive optical detector, etc.

During operation, the light sources 204 will direct light via the waveguides 208 to illuminate the sample in detecting chambers 106. The light detectors 206 will detect the light via the waveguides 210 passing through the sample in detecting chambers 106. Thus, the waveguides 208 and 210 serve to propagate light from/to the light sources 204 and light detectors 206. According to an exemplary embodiment, waveguides 208 and 210 are commercially-available flexible polymer waveguides.

According to an alternative embodiment, the waveguides 208 and 210 are located on the same side of the detecting chambers 106. See, for example, device 300 of FIG. 3. The components in common with device 100 of FIG. 1 and FIG. 2 are numbered alike in FIG. 3. In this example, however, the waveguides 208 (for illumination) and 210 (for detection) are located on the same side of the detecting chambers 106 as one another. A reflector 302 is present on a side of the detecting chambers 106 (in this example under the detecting chambers 106) opposite the waveguides 208/210). The reflector 302 can be a metalized mirror surface to reflect the light back. Suitable materials for the reflector include, but are not limited to, stainless steel, aluminum, silicon, ceramic, glass, polycarbonate, PET, PEN coated with metal. In this example, only the top surface of the detecting chambers 106 are optically clear. Both illumination and detection waveguides 208 and 210 are installed on the top surface, and are coupled to light source and detector (spectrometer). It is notable that waveguides 208 and 210 are separate waveguides and that the light source 204 is separate from the light detector 206.

In another exemplary embodiment, the mixing and detecting are performed in a single chamber. See, for example, device 400 shown in FIG. 4 (top-down view) and FIG. 5 (side view). Like the embodiments above, device 400 includes a main sample transport region 401 (with intake ports 101a and 101b) at the entrance to multiple fluidic channels 402. In this example, however, the mixing and detecting chambers are combined into mixing and detecting chambers 404. Thus, as described above, mixing of the reagent(s) with the sample occurs in chambers 404. Optical detection of the sample takes place in the same chambers 404.

A vent 408 present at the end of each of the mixing/detecting chambers 404 removes air and allows the flow of fluid into the respective chambers. Liquid blockers 410 are inserted after the mixing/detecting chambers 404 before the opening of the vent 408 to restrict the flow of liquid out from the vent 408. The liquid blockers 410, however, permit air to pass through.

Figure 5:
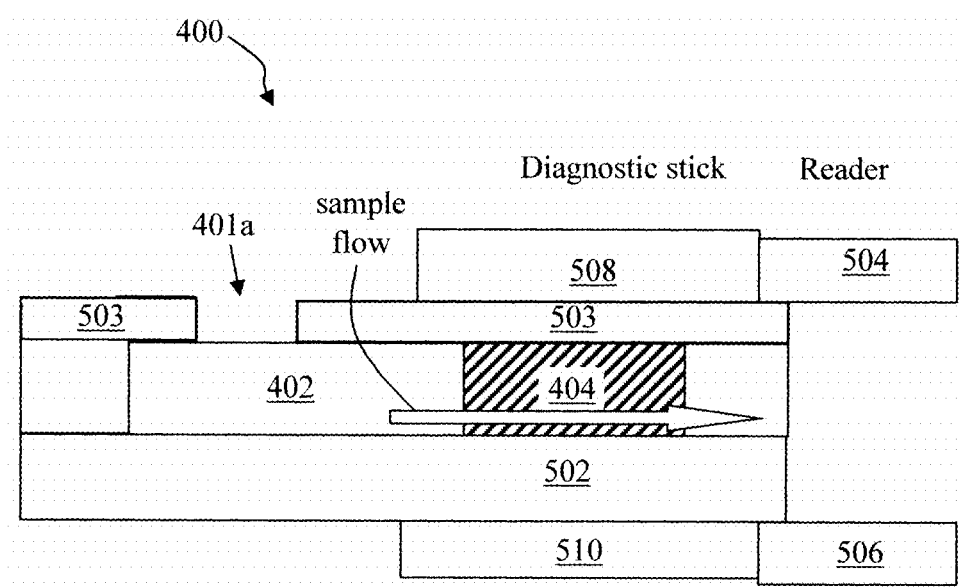
FIG. 5 is a side view diagram of the diagnostic device of FIG. 4 according to an embodiment of the present invention.

From the side view of device 400 shown in FIG. 5, it can be seen that the intake port 401a, fluidic channels 402, and the mixing/detecting chambers 404 are oriented alongside one another on a substrate 502. Suitable substrate materials were provided above. Further, as shown in FIG. 5, a cover 503 is present over, and sealing the fluidic channels 402 and the mixing/detecting chambers 404.

As shown in FIG. 5, the spectrometer ("Reader") component includes at least one light source 504 and at least one light detector 506 that are coupled to the mixing/detecting chambers 404 via waveguides 508 and 510, respectively. Waveguides 508 and 510 transmit and receive light from/to the light source 504 and the light detector 506, respectively. In the exemplary embodiment shown in FIG. 5, the waveguides 508 and 510 are located on opposite sides, e.g., above and below, the detecting chambers 404, respectively. However, in the same manner as provided above, embodiments are also contemplated herein where the waveguides are located on the same side of the mixing/detecting chambers 404, and reflective optical readings are made.

Figure 4:
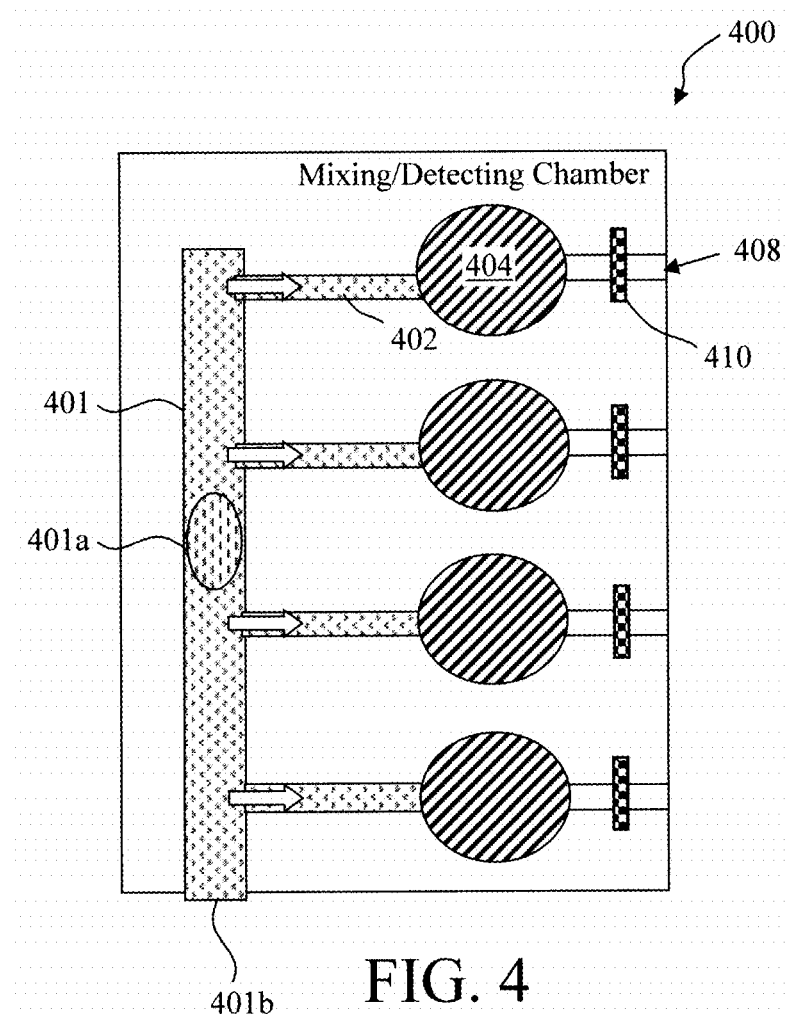
FIG. 4 is a top-down diagram of an exemplary diagnostic device having combined mixing and detecting chambers according to an embodiment of the present invention.

For the configuration shown in FIG. 4 and FIG. 5 where the mixing chamber and detection chamber are combined, the light source 504 and the light detector 506 in the reader can be used to measure the change in light transmission when the sample liquid reaches the combined chamber because the presence of the liquid will change the optical property between the substrate 502 and cover 503 and the combined mixing and detection chamber, hence changing the light detected by the light detector 506. In some applications it is desirable to determine when the sample fluid and reagents start to react and to deduce the reaction time.

Figure 6:
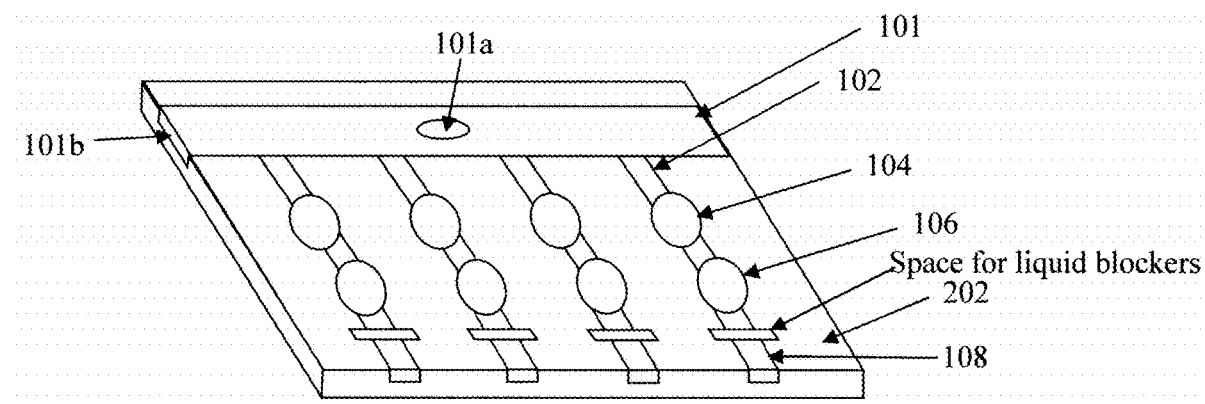
FIG. 6 is a diagram illustrating fluidic channels, mixing chambers, and detecting chambers, vents and fluid blockers having been formed in a substrate according to an embodiment of the present invention.

FIGS. 6-10 illustrate an exemplary methodology for forming device 100, using the two (i.e., mixing and detecting) chamber configuration as an example. As shown in FIG. 6, the process begins with forming the fluidic channels 102, the mixing chambers 104, and the detecting chambers 106, space for the liquid blockers 110 (i.e., space for inserting the liquid blockers 110 into the fluidic channels 102, and vents 108, in the substrate 202. According to an exemplary embodiment, the substrate 202 is polyester, polyethylene Terephthalate (PET), polyethylene Naphthalate (PEN), glass, and/or polycarbonate, and the fluidic channels 102, the mixing chambers 104, the detecting chambers 106, space for the liquid blockers 110 and the vents 108 are formed using a plastic injection molding, hot embossing, photolithography, 3D printing, thermal or UV curable polymer dispensing or screen printing, lamination, or other thermoforming process.

Figure 7:
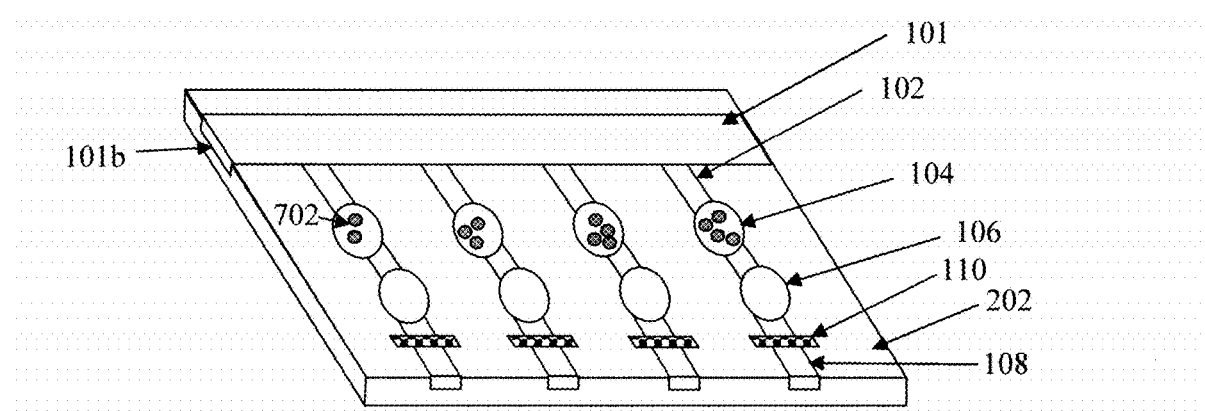
FIG. 7 is a diagram illustrating reagents having been placed in each of the mixing chambers according to an embodiment of the present invention.
Figure 8:
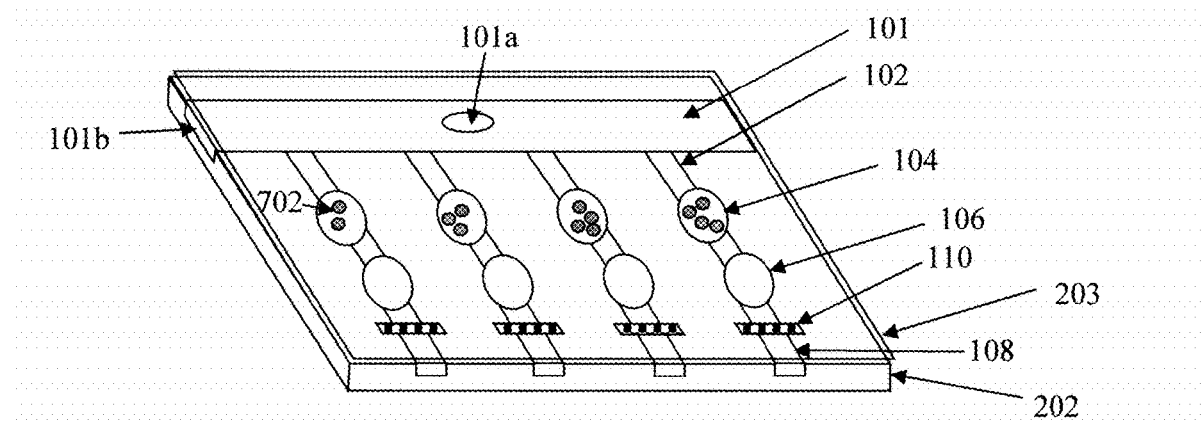
FIG. 8 is a diagram illustrating a cover having been placed over the substrate, sealing the fluidic channels, the mixing chambers, the detecting chambers and the vents, the cover having an intake port present therein according to an embodiment of the present invention.

As shown in FIG. 7, reagents 702 are then placed in each of the mixing chambers 104 and liquid blockers 110 are placed in each of the openings provided for them. The reagents 702 can be introduced to the mixing chambers 104 as a solid or as a liquid solution. When a solution is used (e.g., a solution containing the reagent dissolved or dispersed in a solvent), a drying step is then preferably used to evaporate the solvent, fixing the reagent in the mixing chamber. It is not until the liquid sample enters the mixing chamber during testing that the reagent is released into the sample. In one exemplary embodiment, different reagents 702 are placed in different mixing chambers 104. According to another exemplary embodiment, varying amounts of the reagents 702 are placed in amongst the mixing chambers 104. See, for example FIG. 7 which schematically illustrates successively greater amounts of the reagent 702 being placed into the mixing chambers 104 from left to right.

Varying the amount of the reagents 702 can be used for variable range detection. For instance, if the concentration of analyte is significantly greater than that of the reagent, the reagent can become saturated during testing thereby making it impossible to ascertain the level of the analyte in the sample. Thus, by varying the concentration of the reagent 702 amongst the mixing chambers 104, a range of analyte concentrations can be observed. Further, as will be described in detail below, readings can be taken at the various different reagent concentrations with only the best reading being saved/reported.

A cover 203 is then placed over the substrate 202, sealing the fluidic channels 102, the mixing chambers 104, the detecting chambers 106, and the vents 108. See FIG. 8. Preferably, the cover is formed from a transparent material, such as a polyester, polyethylene Terephthalate (PET), polyethylene Naphthalate (PEN), glass, and/or polycarbonate.

This will permit light (from the light sources 204) to pass through the cover 203 as well as through the detecting chambers 106 and substrate 202 to be picked up by the light detectors 206. The cover 203 includes intake port 101a which is aligned with region 101.

Figure 9:
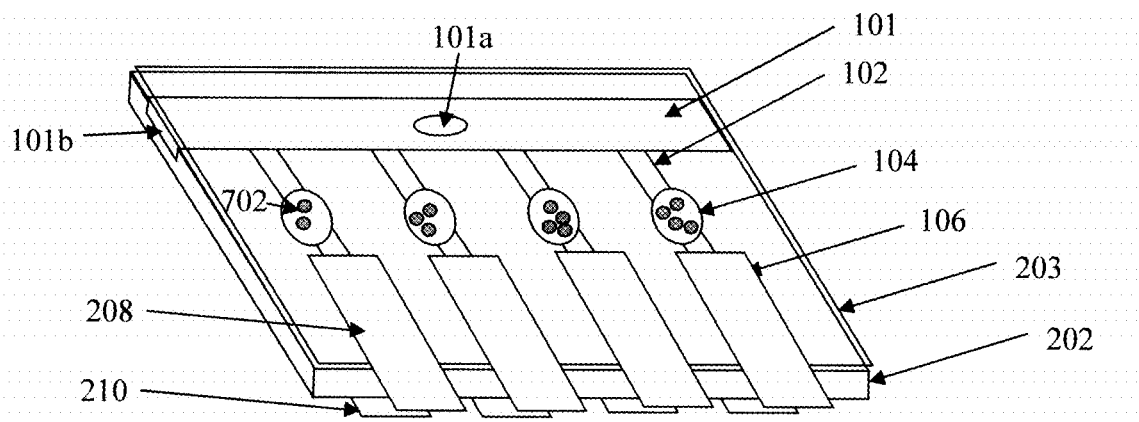
FIG. 9 is a diagram illustrating waveguides having been placed above and below the detecting chambers according to an embodiment of the present invention.

As shown in FIG. 9, the waveguides 208 and 210 are then placed above and below the detecting chambers 106. According to an exemplary embodiment, the waveguides 208 and 210 are attached to the cover 203 (above the detecting chambers 106) and to the substrate 202 (below detecting chambers 106) using an index matching adhesive, such as a clear epoxy or transparent pressure sensitive adhesive.

Figure 10:
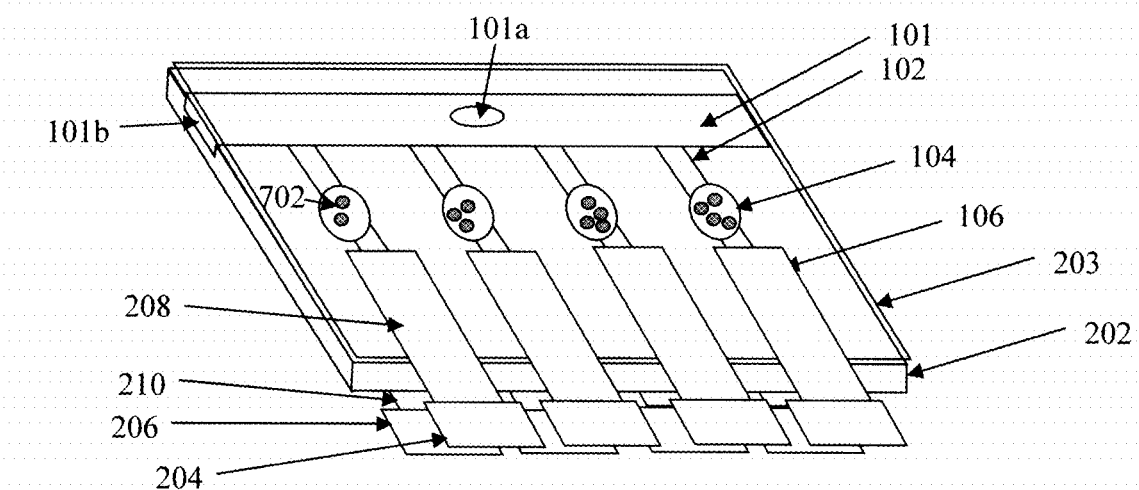
FIG. 10 is a diagram illustrating light sources and light detectors having been coupled to the waveguides according to an embodiment of the present invention.

Finally, as shown in FIG. 10, light sources 204 and light detectors 206 are coupled to the waveguides 208 and 210, respectively. According to an exemplary embodiment, the light sources 204 and light detectors 206 are coupled to the waveguides 208 and 210 using a connector such as butt connectors.

Figure 11:
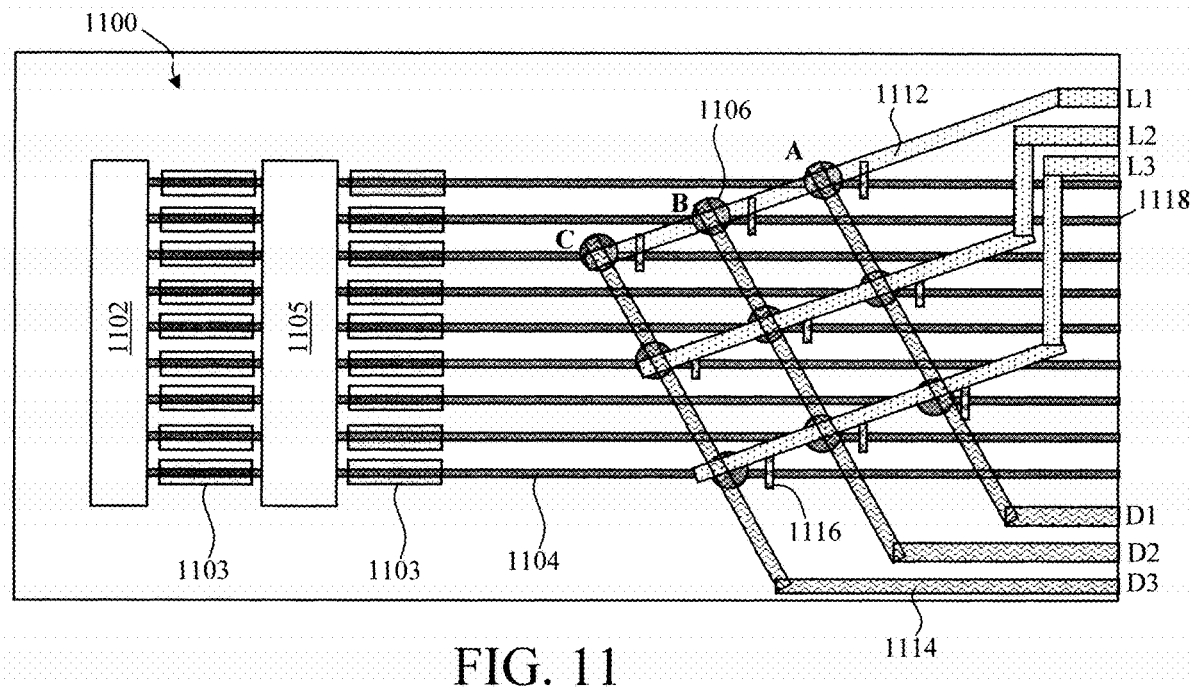
FIG. 11 is a top-down diagram of yet another exemplary diagnostic device with a matrix of mixing/detecting chambers according to an embodiment of the present invention.

A variation of device 100 is shown in FIG. 11 which enables the use of light sources of different wavelengths in combination with light detectors of different sensitivities to test a sample. For instance, diagnostic device 1100 shown in FIG. 11 has a sample intake port 1102 connected by fluidic channels 1104 to multiple detecting chambers 1106. In the same manner as described above, the sample intake port 1102, fluidic channels 1104 and mixing/detecting chambers 1106 can be formed using a plastic injection molding, hot embossing, photolithography, 3D printing, thermal or UV curable polymer dispensing or screen printing, or other thermoforming process.

Figure 12:
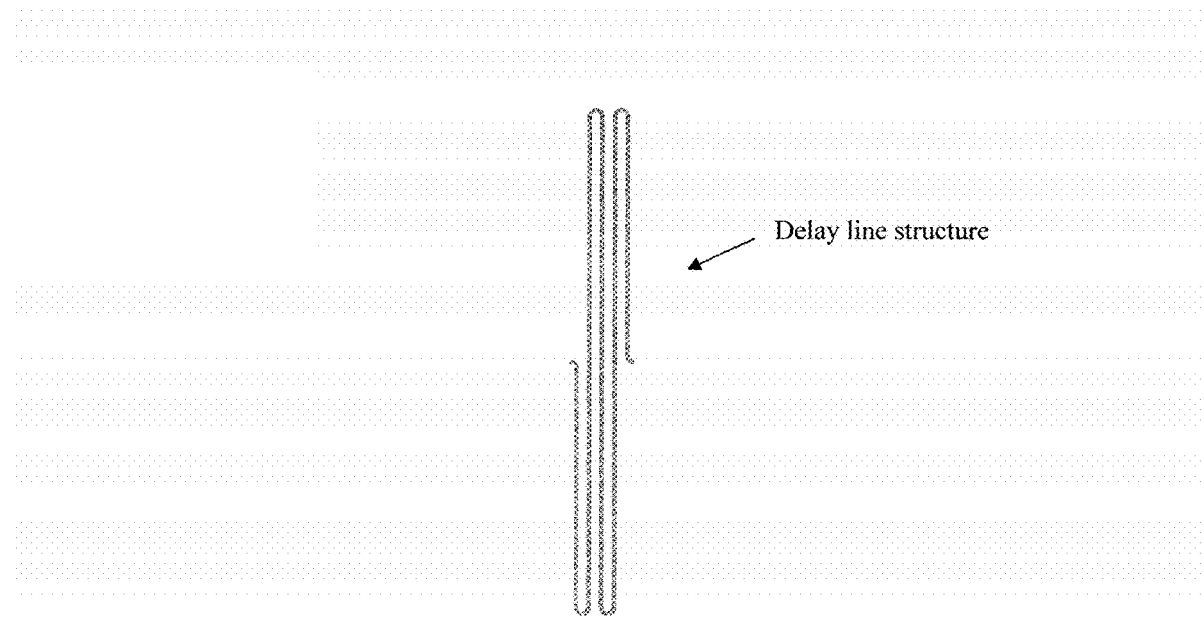
FIG. 12 is a diagram illustrating an exemplary delay line structure according to an embodiment of the present invention.

In this particular example, the sample intake port 1102 will deliver the fluidic samples, either by injection or capillary action, to the fluidic channels 1104 which transport the sample to the mixing/detecting chambers 1106. Optionally, a delay element 1103 and/or a filter 1105 can be inserted in the fluidic channels 1104 for pre-detection sample treatment. By way of example only, pre-detection sample treatment might involve separating and removing cells. The delay element 1103 can slow down the flow for better filtration. In addition, some samples, such as blood, might need to be stabilized to accurate analysis. As shown in FIG. 11, the delay element 1103 can be inserted before and/or after the filter 1105. By way of example only, the delay element 1103 can be a narrower fluidic channel or, as shown in FIG. 12, a lengthy channel in the form of serpentine lines. By way of example only, the filter can be a trap, well, membrane, a filter paper, a porous media, etc.

The example in FIG. 11 is of a device with combined mixing and detection chambers. During operation, the sample fluid delivered via the fluidic channels 1104 fills the mixing/detecting chambers 1106 and is stopped by liquid blockers 1116 so that the sample inside the mixing/detecting chambers 1106 will not be diluted by the continuous flow. As highlighted above, the liquid blockers can be a porous material or membrane is gas permeable but does not pass liquid or has high flow resistance to liquid. Vents 1118 are present at a distal end of the fluidic channels 1104 opposite the intake port 1102. The vents 1118 permit capillary action to drive the fluid sample from the intake port 1102 to the mixing/detecting chambers 1106. Waveguide 1112 and 1114 are laminated on opposite side of the substrate to couple to the light source and light detection apparatus, respectively (as described above). It is notable that the routing of the waveguides is illustrated schematically in the figures, and in practice the waveguides would have gradual curves rather than sharp bends.

Further, FIG. 11 illustrates an example of a 3×3 matrix mixing/detecting chamber configuration. Each waveguide 1112 that connects to a light source (e.g., light source L1, L2, L3, etc.) delivers light to three mixing/detecting chambers 1106, and each waveguide 1114 that connects to a light detector (e.g., light detector D1, D2, D3, etc.) detects the optical output from three mixing/detecting chambers 1106. The advantages of the matrix configuration are form factor reduction and hardware reduction. In the 3λ3 matrix that is illustrated in FIG. 11, only 3 light detector and light source pairs are needed for 9 detection chambers. For instance, mixing/detecting chamber A is present at the intersection of a waveguide 1112 coupled to light source L1 and a waveguide 1114 coupled to light detector D1, whereas mixing/detecting chamber B is present at the intersection of a waveguide 1112 coupled to the light source L1 and a waveguide 1114 coupled to a light detector D2.

In operation, only a single one of the light sources is active at a given time, so that each light detector is only receiving a signal from a single mixing/detecting chamber 1106. According to an exemplary embodiment, the light sources are activated sequentially to illuminate each of the mixing/detecting chambers 1106 in sequence. When light source L1 is on, it illuminates mixing/detecting chambers A, B and C. The light detectors D1, D2, D3, etc. can be programed to take optical measurement for the three mixing/detecting chambers that are illuminated. The procedure repeats for the next row of mixing/detecting chambers when they are illuminated by the next light (e.g., L2) via the respective waveguide 1112. It is notable that each light source can be a single LED or a collection of LEDs with different wavelengths, or a light source with broad spectrum, or a laser. If the light source is a collection of the LEDs with different wavelengths, the light source can be programed to turn on a specific LED only with the wavelength of light that is best suited for the specific analyte targeted in the given mixing/detecting chamber. As provided above, suitable light detectors include, but are not limited to, photodiodes, a photomultiplier tube, a CCD or CMOS imager, and/or a wavelength-sensitive optical detector.

Figure 13:
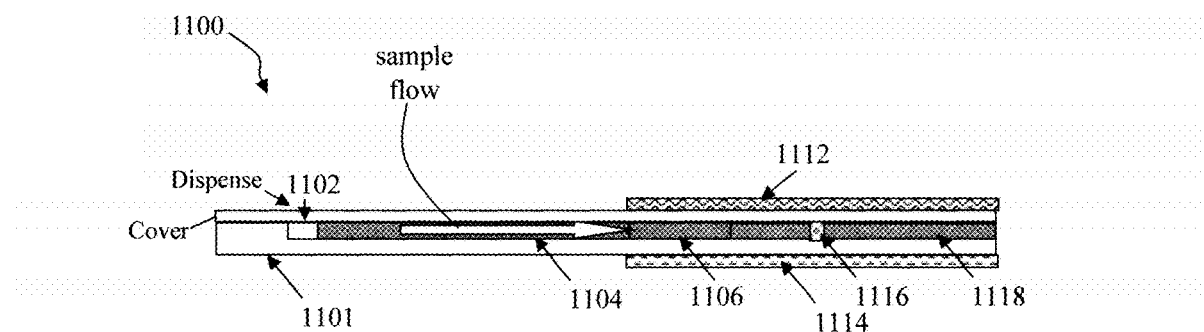
FIG. 13 is a side-view diagram of the diagnostic device of FIG. 11 according to an embodiment of the present invention.

FIG. 13 is a side view diagram of diagnostic device 1100. As shown in FIG. 13, the intake port 1102, the fluidic channels 1104, mixing/detecting chambers 1106, fluid blockers 1116 and vent 1118 are formed in a substrate 1101. A sample deposited into the intake port 1102 flows through the fluidic channels 1104 and into the mixing/detecting chambers 1106 where light introduced by waveguide 1112 (from a light source) is passed through the sample and is transmitted via waveguide 1114 to a light detector.

Figure 14:
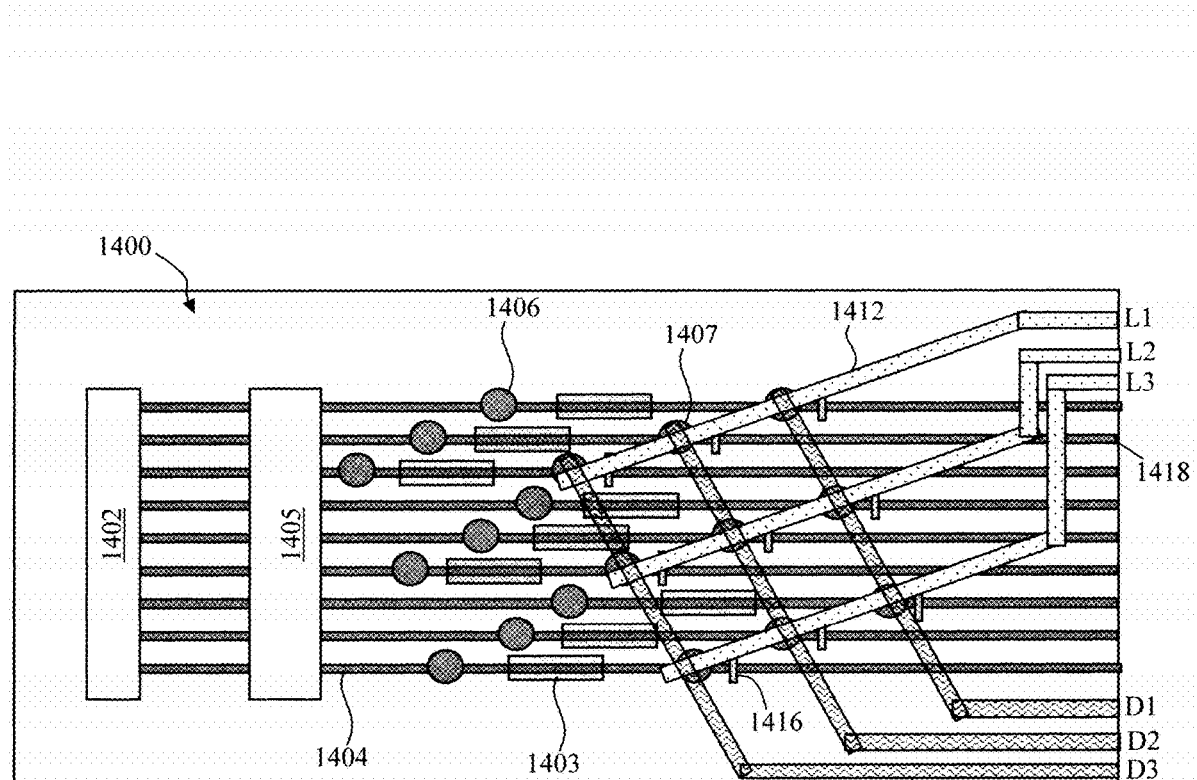
FIG. 14 is a top-down diagram of a variant of the diagnostic device with separate mixing chambers and a matrix of detecting chambers according to an embodiment of the present invention.

A variation of the device in FIG. 11 having separate mixing and detection chambers is shown in FIG. 14. Diagnostic device 1400 shown in FIG. 14 has a sample intake port 1402 connected by fluidic channels 1404 to multiple mixing chambers 1406 and multiple detecting chambers 1407. Optionally, a delay element 1403 and/or a filter 1405 can be inserted in the fluidic channels 1404 for pre-detection sample treatment. By way of example only, the delay element 1403 can be a lengthy channel in the form of serpentine lines. See, for example, FIG. 12—described above.

Vents 1418 lead away from the detecting chambers 1407 to permit capillary action to drive the fluid sample from the intake port 1402 to the mixing chambers 1406 and detecting chambers 1407, however liquid blockers 1416 are present between the detecting chambers 1407 and the opening of the vents 1418 so that the sample inside the detecting chambers 1407 will not be diluted by the continuous flow. Waveguides 1412 and 1414 couple multiple light sources (L1, L2, L3, etc.) and multiple light detectors (D1, D2, D3, etc.) to multiple detection chambers 1407.

During operation, the fluid sample flows into the mixing chambers 1406, mixes and reacts with reagent(s), then flows into detection chambers 1407 for optical measurement. As shown in FIG. 14, a delay element 1403 can be inserted in between the mixing chambers 1406 and the detecting chambers 1407 if a certain reaction time is needed. The optical measurement operation is the same as described above.

Figure 15:
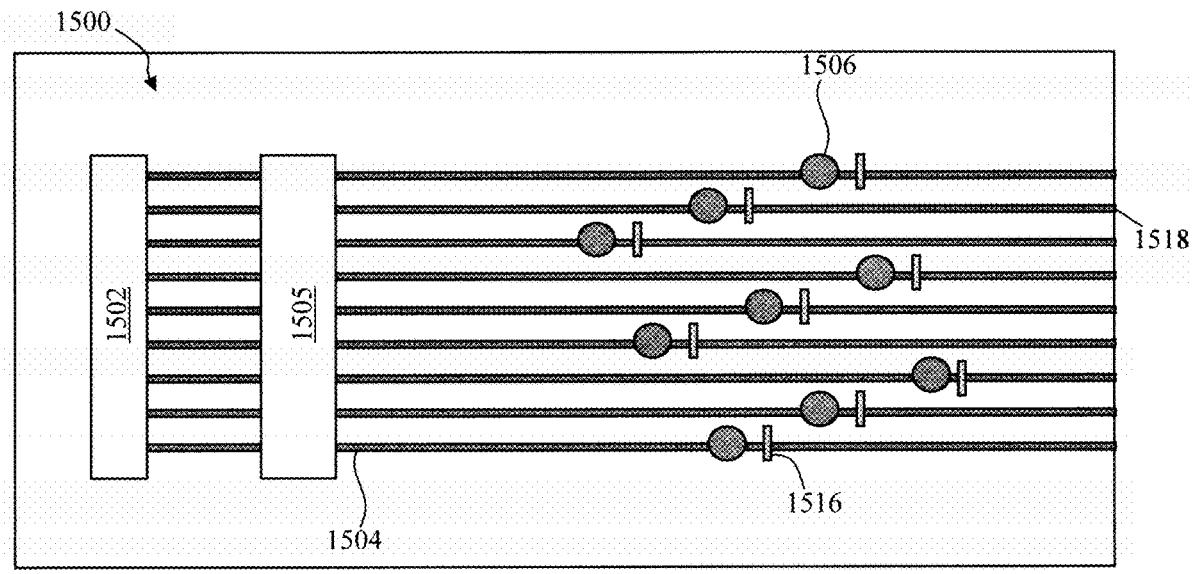
FIG. 15 is a top-down diagram of still yet another exemplary diagnostic device for optical detection using a light source and camera according to an embodiment of the present invention.

Embodiments are also contemplated herein where the optical measurements are made using at least one multi-wavelength light source and a monochromatic detection camera. See, for example, FIG. 15 (top-down view) and FIG. 16 (side view) of diagnostic device 1500. As shown in FIG. 15, diagnostic device 1500 has a sample intake port 1502 connected by fluidic channels 1504 to multiple mixing/detecting chambers 1506 (through an optional filter 1505). Vents 1518 lead away from the mixing/detecting chambers 1506 to permit capillary action to drive the fluid sample from the intake port 1502 to the mixing/detecting chambers 1506, however liquid blockers 1516 are present between the mixing/detecting chambers 1506 and the opening of the vents 1518 so that the sample inside the mixing/detecting chambers 1506 will not be diluted by the continuous flow.

Figure 16:
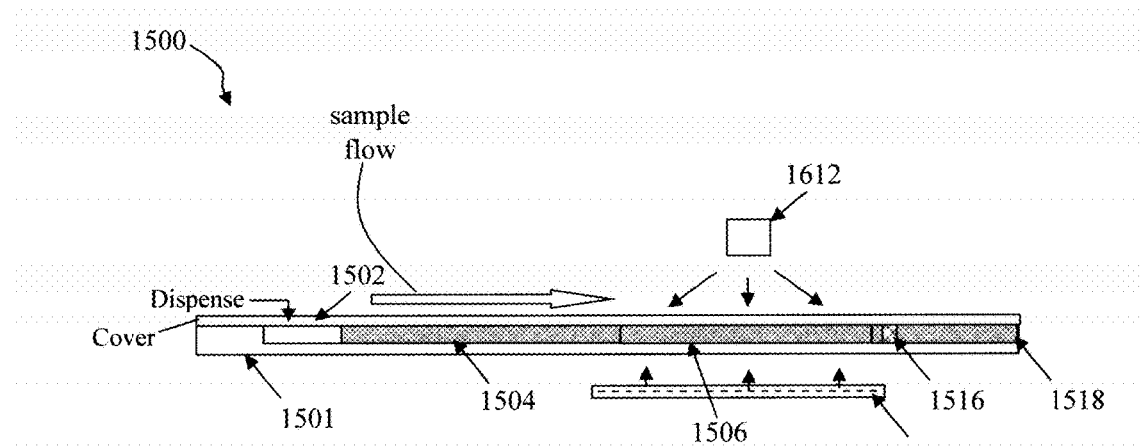
FIG. 16 is a side view diagram of the diagnostic device of FIG. 15 according to an embodiment of the present invention.

FIG. 16 is a side view diagram of diagnostic device 1500. As shown in FIG. 16, the intake port 1502, the fluidic channels 1504, mixing/detecting chambers 1506, fluid blocker regions 1516 and vent 1518 are formed in a substrate 1501. Rather than employing light source/detector and waveguides as above, in this exemplary embodiment, a camera 1612 is positioned above the mixing/detecting chambers 1506 in order to capture images of the samples in the mixing/detecting chambers 1506 while the mixing/detecting chambers 1506 are illuminated from below via one or more light sources 1514, i.e., single or multiple wavelength light sources. See FIG. 16.

According to an exemplary embodiment, the camera 1512 is a monochromatic digital camera such as the Omnivision OV6922 2.5 micrometer (μm) pixel size camera on a chip available from OmniVision Technologies, Inc., Santa Clara, Calif. The light source(s) 1514 preferably is/are adjustable to provide light of various wavelengths. In the example above, different light sources were used to illuminate the sample with different wavelengths of light. Here the process is simplified through the use of a single light source that can be tuned to vary the wavelength of light it produces. As highlighted above, using different wavelengths of the light source is advantageous because different reagent and analyte detection methods might be optimized for different wavelengths.

Figure 17:
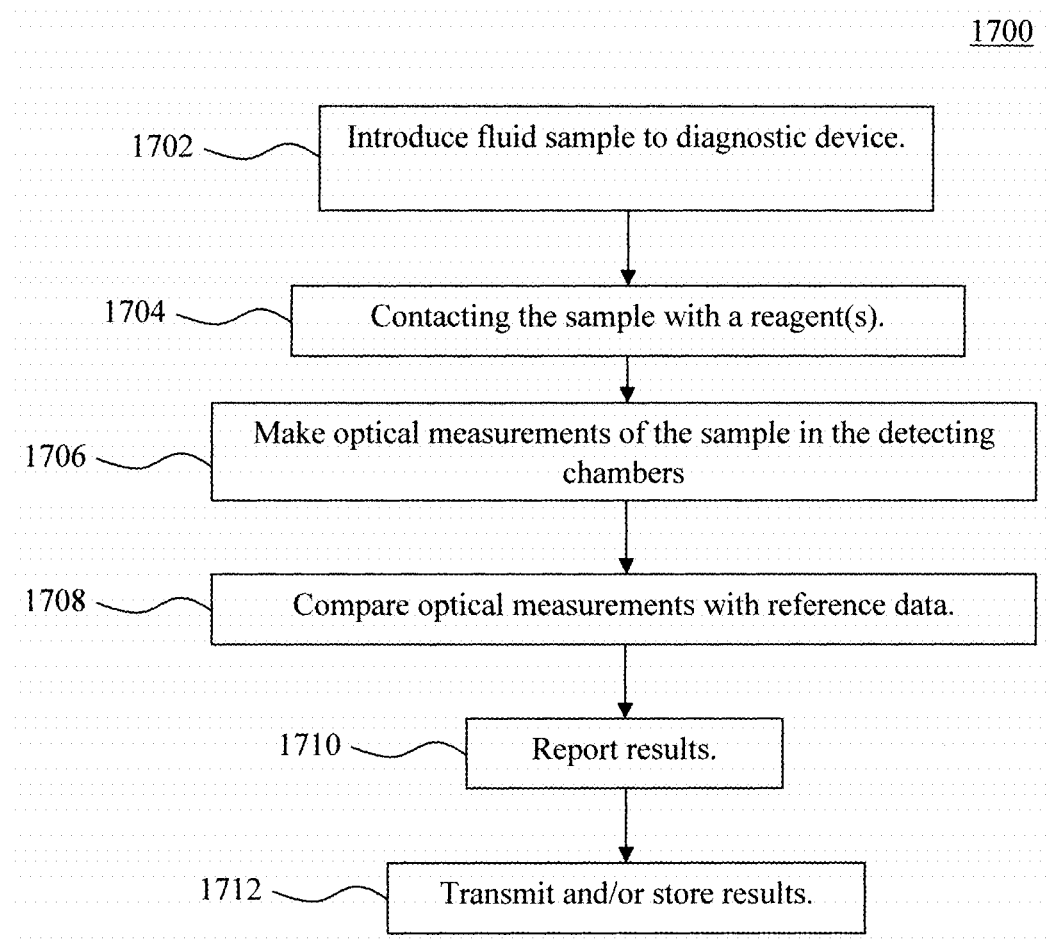
FIG. 17 is a diagram illustrating an exemplary methodology for using the present diagnostic devices for analyzing a fluid sample according to an embodiment of the present invention.

FIG. 17 is a diagram illustrating an exemplary methodology 1700 for using the present diagnostic devices for analyzing a fluid sample. As provided above, the present techniques can be implemented in a variety of different testing scenarios and settings. For instance, the fluid sample can be a medical specimen (e.g., for urinalysis), a biological and/or chemical sample, a sample collected in the field (such as a water sample), etc.

In step 1702, the fluid sample is introduced to the device. For instance, a user can deposit the fluid sample into the intake port at the opening to the fluidic channels of the device. See, for example, intake ports 101a,b, 401a,b, 1102, 1402, 1502 in devices 100, 300, 400, 1100, 1400, and 1500, respectively.

In step 1704, the fluid sample is contacted with at least one reagent. By way of example only, as described above the reagents can be contained in one or more mixing chambers (see, for example, mixing chambers 104 and 1406 in devices 100/300 and 1400, respectively) or combined mixing/detecting chambers (see, for example, mixing/detecting chambers 404, 1106, 1506 in devices 400, 1100, 1500, respectively). As also described above, when multiple reagents are employed the reagents can be selective for different analytes and/or can be used in varying concentrations for variable range detection. Thus, according to one exemplary embodiment step 1704 involves (separately) contacting the fluid sample with at least two different reagents specific for at least two different target analytes. To use a simple example to illustrate this concept, if the fluid sample is for a urinalysis test, then one reagent (e.g., glucose oxidase) might target glucose detection, while another reagent (e.g., sodium nitroprusside) targets ketones. According to another exemplary embodiment, step 1704 involves (separately) contacting the fluid sample with at least two different amounts of the same reagent. That way, the range of detection can be expanded. For instance, as described above, by varying the dye/reagent ratio amongst the mixing chambers, a range of analyte concentrations can be observed.

By having multiple mixing and/or detecting chambers, each having a different reagent or different amounts of reagent can be used to separately contact the fluid sample with the reagents. According to an exemplary embodiment, when separate mixing and detecting chambers are present, an equal number of detection chambers is used to separately analyze each sample (i.e., there is a 1:1 correlation between the number of mixing chambers and detecting chambers in the device). By passing the sample through the mixing chambers on its way to the detecting chambers, the sample will contact the reagent(s) in the mixing chambers before passing into the detecting chambers where the sample is analyzed optically.

In the embodiments presented above, each of the device configurations contains at least one detection chamber or combined mixing/detecting chamber into which the sample which has been contacted with the reagent(s) flows for analysis and detection.

Namely, in step 1706, optical measurements are made of the fluid sample in the detecting (or combined mixing/detecting) chamber(s). A variety of different spectrometer designs are contemplated herein for making optical measurements of the fluid sample. By way of example only, in one exemplary embodiment, at least one light source and at least one light detector are used to transmit/detect light that has passed through the sample in the detecting chamber(s). In that case, the light from the light source(s) is carried to the detecting chamber(s) by the (transmission) waveguides. The light then passes through the sample in the detecting chamber(s), where it is transmitted, via the (detecting) waveguides, to the light detector(s). As described above, the waveguides coupling the light source(s) and the light detector(s) to the detecting chambers can be on opposite sides of the detecting chamber(s) from one another, or on the same side of the detecting chamber(s) (and measurements made using a reflector).

In another exemplary embodiment, a digital camera and light source are located above and below the detecting chamber(s) respectively. In that case, light of a given wavelength, generated using the light source, is used to illuminate the sample in the detecting chambers. Digital images of the sample are then obtained using the digital camera.

In the case when a combined mixing/detecting chamber is used, the point in time when the fluid sample reaches the mixing/detecting chamber (see step 1704), and the reaction between the reagent and analyte starts can be determined as described above using the change in optical signal. The reaction time can be used to determine when to perform the optical measurements in step 1706, or in the comparison of the optical measurements with reference data, in step 1708.

Data extracted from the sample via the light detector(s) or digital camera can then be processed and used in a number of different ways. For instance, in step 1708 readings from the light detector(s) or digital camera can be compared to reference data taken from samples having the target analyte at known concentrations. For instance, the readings from the light detector(s) can be compared with those taken from the known samples, as can the images obtained from the digital camera (e.g., via image matching techniques).

The results can be reported to the user (see step 1710) and/or transmitted to one or more other users for storage and/or analysis (see step 1712). For instance, methodology 1700 may be performed to analyze a sample from a patient, and in step 1710 the results are provided to the patient, e.g., via a display on the device itself and/or transmitted to a mobile device of the user, etc. The results may also be transmitted in step 1712 to other users, such as the patient's doctor for consultation, and/or be recorded, e.g., in the patient's electronic medical file.

As provided above, in the case of a device having a matrix of detecting chambers (see, for example, devices 1100 and 1400) only a single one of the light sources is active at a given time, so that each light detector is only receiving a signal from a single mixing/detecting chamber. According to an exemplary embodiment, the light sources are activated sequentially to illuminate each of the mixing/detecting chambers in sequence. When a given light source is on, it illuminates the mixing/detecting chambers to which it is coupled. The light detectors can be programed to take optical measurements for the mixing/detecting chambers that are illuminated. The procedure then repeats for the next row of mixing/detecting chambers when they are illuminated by the next light source. This process is described in further detail by way of reference to FIG. 18.

Figure 18:
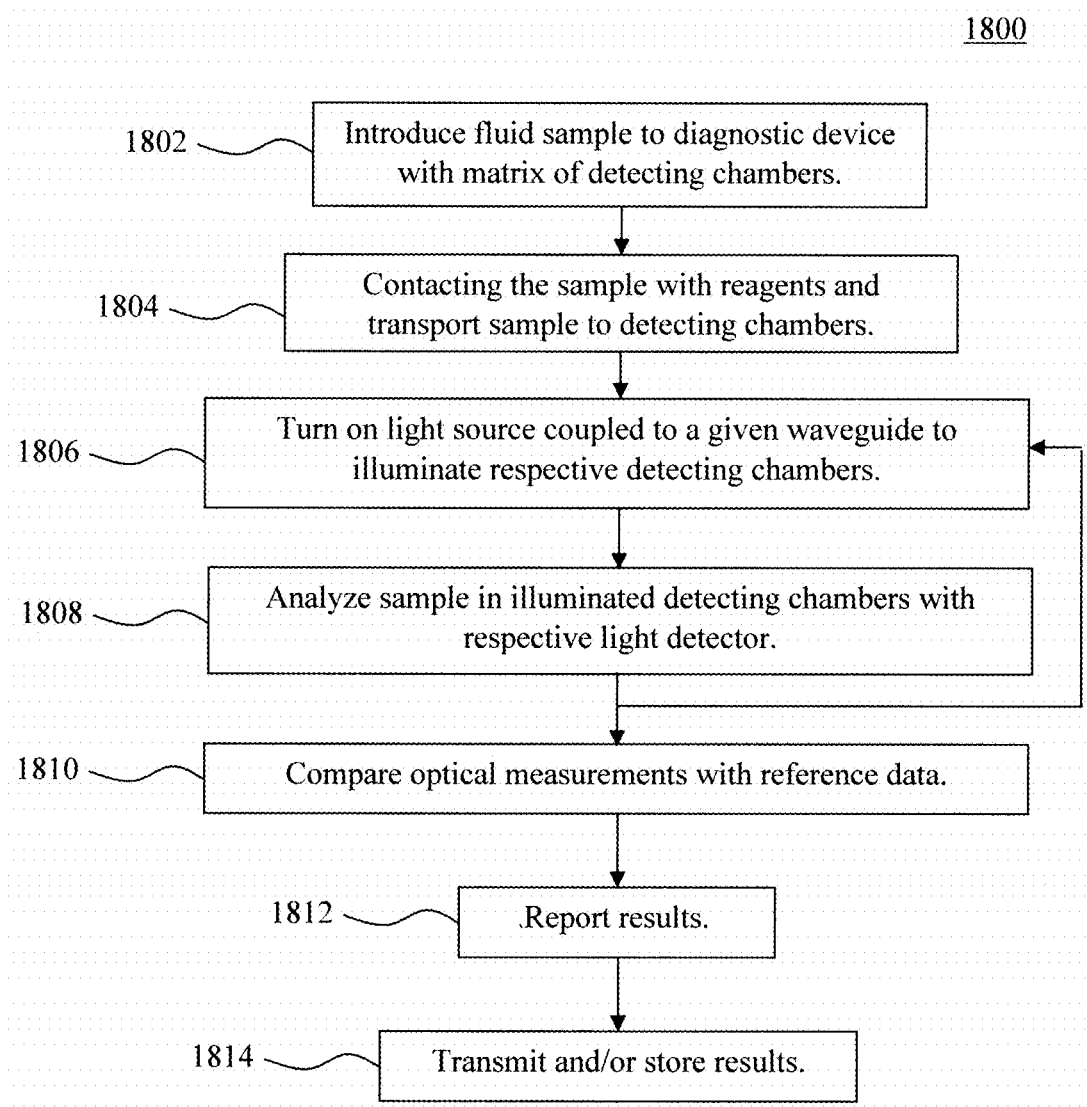
FIG. 18 is a diagram illustrating an exemplary methodology for using the present diagnostic device having a matrix of detecting chambers for analyzing a fluid sample according to an embodiment of the present invention.

FIG. 18 is a diagram illustrating an exemplary methodology 1800 for using the present diagnostic device with a matrix of detecting chambers for analyzing a fluid sample. In step 1802, the fluid sample is introduced to the device. In step 1804, the fluid sample is contacted with reagents and transported to the detecting chambers. By way of example only, as described above the reagents can be contained in one or more mixing chambers or in combined mixing/detecting chambers.

In step 1806, a given one of the light sources is turned on to illuminate the detecting chambers to which the given light source is coupled (by its respective waveguide). In step 1808, the sample in the illuminated detecting chambers is analyzed using the light detectors coupled to those detecting chambers (by their respective waveguides). Steps 1806 and 1808 are then repeated to collect optical measurement data from the next row of detecting chambers via the next light source and respective light detectors, until data has been extracted from all of the detecting chambers The data extracted from the sample via the light detectors can then be processed and used in a number of different ways. For instance, in step 1810 readings from the light detectors can be compared to reference data taken from samples having the target analyte at known concentrations. The results can be reported to the user (see step 1812) and/or transmitted to one or more other users for storage and/or analysis (see step 1814).

FIG. 19 provides some illustrative non-limiting examples of reagents and target analytes that may be implemented in accordance with the present techniques. Also provided in FIG. 19 is the incubation time (i.e., the time needed for the reagent to react with the target analyte).

Figure 20:
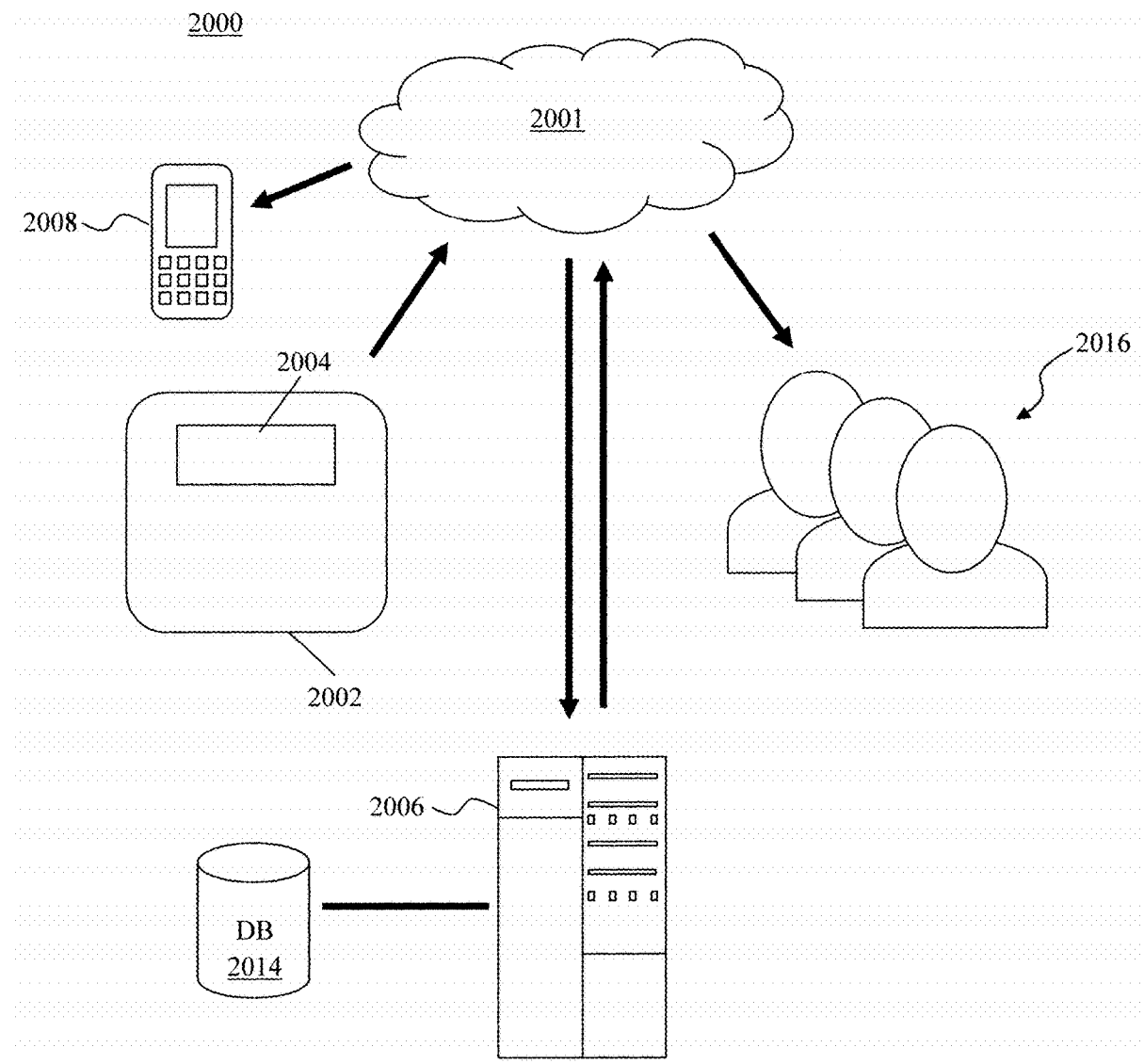
FIG. 20 is a diagram illustrating an exemplary diagnostic system according to an embodiment of the present invention.

FIG. 20 is a diagram illustrating an exemplary diagnostic system 2000. As shown in FIG. 20, system 2000 includes at least one of the present diagnostic devices 2002 with spectrometer which, as per methodology 1700 and/or methodology 1800, is used to analyze a fluidic sample. Diagnostic device 2002 is generally representative of any of the design configurations provided above. As shown in FIG. 20, diagnostic device 2002 can include a display 2004. The diagnostic device 2002 can also be in communication with a data management system 2006 (via cloud 2001). Data management system 2002 is configured to receive the data collected by the diagnostic device 2002, process/analyze the data, and generate electronic records such as EMRs stored, for example, in a database DB 2014.

As shown in FIG. 20, data management system 2006 can also be accessed by one or more other users 2016. For instance, when the fluidic sample is collected from a patient, other users that might be interested in the results can include the doctor and/or hospital treating the patient. Optionally, the system 2000 can also permit communication between the diagnostic device 2002 and one or more mobile devices 2008 such as the user's smartphone.

Figure 21:
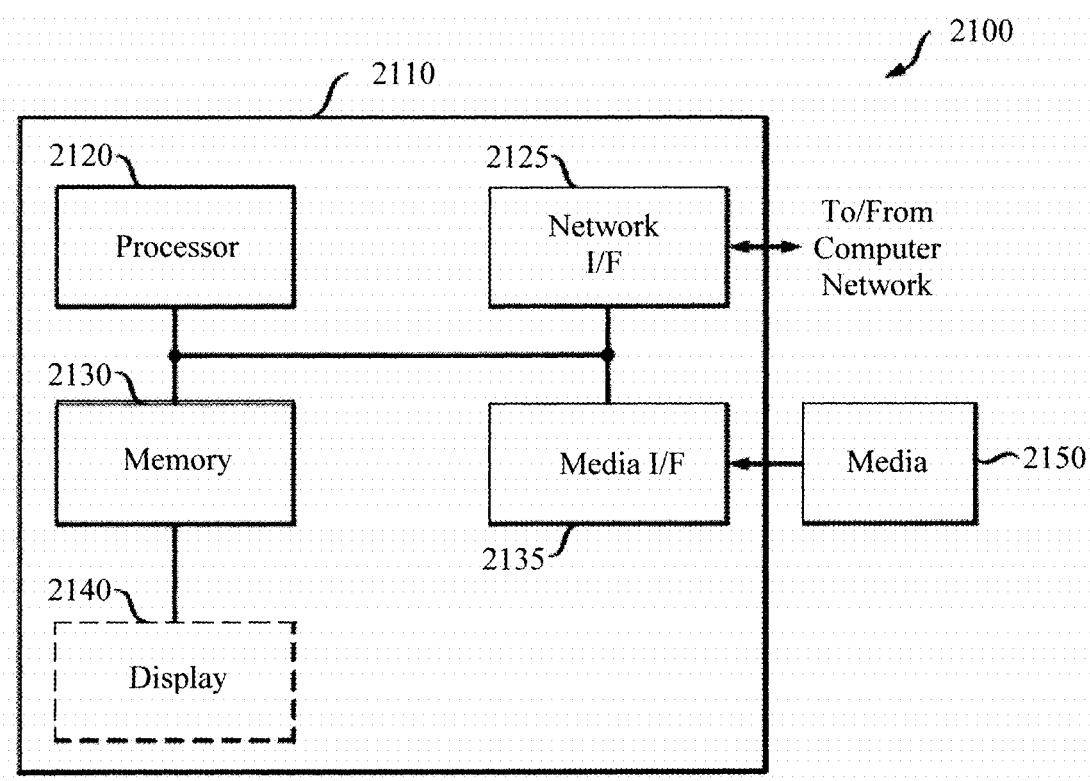
FIG. 21 is a diagram illustrating an exemplary apparatus that can be configured to implement one or more of the methodologies presented herein according to an embodiment of the present invention.

Turning now to FIG. 21, a block diagram is shown of an apparatus 2100 that can be configured to perform one or more of the methodologies presented herein. For example, apparatus 2100 can serve as the data processing apparatus 2006 in system 2000 and can be configured to perform one or more of the steps of methodology 1700 (of FIG. 17) or methodology 1800 (of FIG. 18) described above. Apparatus 2100 includes a computer system 2110 and removable media 2150. Computer system 2110 includes a processor device 2120, a network interface 2125, a memory 2130, a media interface 2135 and an optional display 2140. Network interface 2125 allows computer system 2110 to connect to a network, while media interface 2135 allows computer system 2110 to interact with media, such as a hard drive or removable media 2150.

Processor device 2120 can be configured to implement the methods, steps, and functions disclosed herein. The memory 2130 could be distributed or local and the processor device 2120 could be distributed or singular. The memory 2130 could be implemented as an electrical, magnetic or optical memory, or any combination of these or other types of storage devices. Moreover, the term "memory" should be construed broadly enough to encompass any information able to be read from, or written to, an address in the addressable space accessed by processor device 2120. With this definition, information on a network, accessible through network interface 2125, is still within memory 2130 because the processor device 2120 can retrieve the information from the network. It should be noted that each distributed processor that makes up processor device 2120 generally contains its own addressable memory space. It should also be noted that some or all of computer system 2110 can be incorporated into an application-specific or general-use integrated circuit.

Optional display 2140 is any type of display suitable for interacting with a human user of apparatus 2100. Generally, display 2140 is a computer monitor or other similar display.

Figure 22:
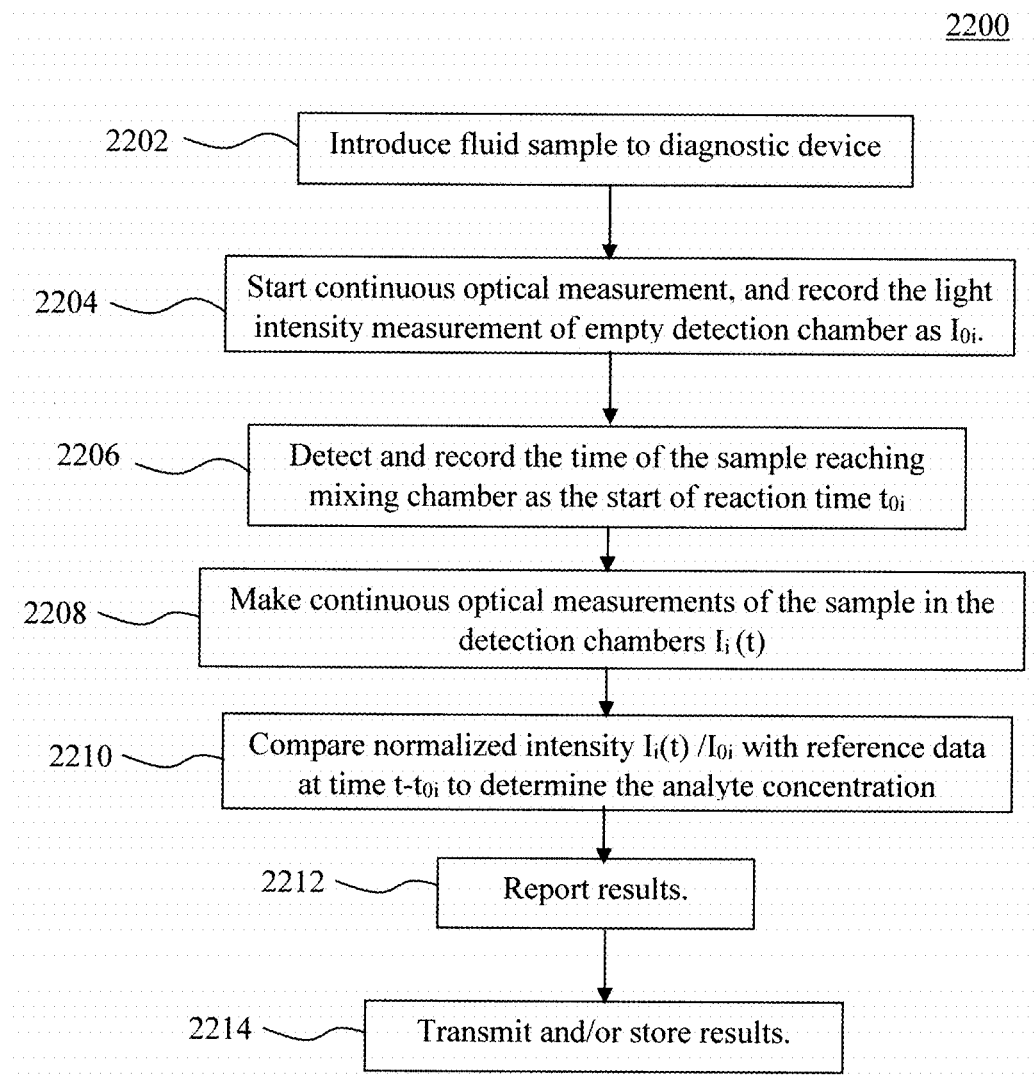
FIG. 22 is a diagram illustrating an exemplary methodology for using the present diagnostic devices for analyzing a fluid sample according to an embodiment of the present invention.

FIG. 22 is a diagram illustrating an exemplary methodology 2200 for using the present diagnostic devices for analyzing a fluid sample. As provided above, the present techniques can be implemented in a variety of different testing scenarios and settings. For instance, the fluid sample can be a medical specimen (e.g., for urinalysis), a biological and/or chemical sample, a sample collected in the field (such as a water sample), etc.

In step 2202, the fluid sample is introduced to the device and optical measurements start. For instance, a user can deposit the fluid sample into the intake port at the opening to the fluidic channels of the device. See, for example, intake ports 101a,b, 401a,b, 1102, 1402, 1502 in devices 100, 300, 400, 1100, 1400, and 1500, respectively.

In step 2204, optical measurement starts immediately after sample is introduced to the device. The optical measurement comprises turning on the light sources, coupling light to the mixing and detecting chambers, measuring light intensity passing through the mixing and detecting chambers by optical detectors. The empty detecting chamber readings prior to the arrival of the sample is stored as $I_{0i}$ for the ith chamber and used to normalize light intensity measurement with the sample for the corresponding chamber.

In step 2206, the event of a fluid sample entering a mixing chamber is detected by the change in light intensity. The time of contact is recorded as $t_{0i}$ for the ith chamber, which will be used to calculate the reaction time at the time of the detection t. Reaction time is $t-t_{0i}$, which will be used to compare with reference data to infer the analyte concentration. The analyte and reagent reaction is time dependent, therefore it is important to compare the light intensity at the same reaction time for better accuracy in concentration detection.

The sample fluid contacts at least one reagent and starts the reaction. By way of example only, as described above the reagents can be contained in one or more mixing chambers (see, for example, mixing chambers 104 and 1406 in devices 100/300 and 1400, respectively) or combined mixing/detecting chambers (see, for example, mixing/detecting chambers 404, 1106, 1506 in devices 400, 1100, 1500, respectively). As also described above, when multiple reagents are employed, the reagents can be selective for different analytes and/or can be used in varying concentrations for variable range detection. Thus, according to one exemplary embodiment step 2206 involves (separately) contacting the fluid sample with at least two different reagents specific for at least two different target analytes. To use a simple example to illustrate this concept, if the fluid sample is for a urinalysis test, then one reagent (e.g., glucose oxidase) might target glucose detection, while another reagent (e.g., sodium nitroprusside) targets ketones. According to another exemplary embodiment, step 2206 involves (separately) contacting the fluid sample with at least two different amounts of the same reagent. That way, the range of detection can be expanded. For instance, as described above, by varying the dye/reagent ratio amongst the mixing chambers, a range of analyte concentrations can be observed.

By having multiple mixing and/or detecting chambers, each having a different reagent or different amounts of reagent can be used to separately contact the fluid sample with the reagents. According to an exemplary embodiment, when separate mixing and detecting chambers are present, an equal number of detection chambers is used to separately analyze each sample (i.e., there is a 1:1 correlation between the number of mixing chambers and detecting chambers in the device). By passing the sample through the mixing chambers on its way to the detecting chambers, the sample will contact the reagent(s) in the mixing chambers before passing into the detecting chambers where the sample is analyzed optically.

In the embodiments presented above, each of the device configurations contains at least one detection chamber or combined mixing/detecting chamber into which the sample which has been contacted with the reagent(s) flows for analysis and detection.

Namely, in step 2208, optical measurements, $I_i(t)$ are made of the fluid sample in the detecting (or combined mixing/detecting) chamber(s) continuously. A variety of different spectrometer designs are contemplated herein for making optical measurements of the fluid sample. By way of example only, in one exemplary embodiment, at least one light source and at least one light detector are used to transmit/detect light that has passed through the sample in the detecting chamber(s). In that case, the light from the light source(s) is carried to the detecting chamber(s) by the (transmission) waveguides. The light then passes through the sample in the detecting chamber(s), where it is transmitted, via the (detecting) waveguides, to the light detector(s). As described above, the waveguides coupling the light source(s) and the light detector(s) to the detecting chambers can be on opposite sides of the detecting chamber(s) from one another, or on the same side of the detecting chamber(s) (and measurements made using a reflector).

In another exemplary embodiment, a digital camera and light source are located above and below the detecting chamber(s) respectively. In that case, light of a given wavelength, generated using the light source, is used to illuminate the sample in the detecting chambers. Digital images of the sample are then obtained using the digital camera.

For the optical measurement taken at time t for ith chamber, $I_i(t)$, the reaction time is $t-t_{0i}$. The normalized intensity is $I_i(t)/I_{0i}$. The normalized intensity at reaction time $t-t_{0i}$ is compared to reference data at time $t-t_{0i}$, to infer the concentration of the analyte in step 2210.

Data extracted from the sample via the light detector(s) or digital camera can then be processed and used in a number of different ways. For instance, in step 2210 readings from the light detector(s) or digital camera can be compared to reference data taken from samples having the target analyte at known concentrations. For instance, the readings from the light detector(s) can be compared with those taken from the known samples, as can the images obtained from the digital camera (e.g., via image matching techniques).

The results can be reported to the user (see step 2212) and/or transmitted to one or more other users for storage and/or analysis (see step 2214). For instance, methodology 2200 may be performed to analyze a sample from a patient, and in step 2212 the results are provided to the patient, e.g., via a display on the device itself and/or transmitted to a mobile device of the user, etc. The results may also be transmitted in step 2214 to other users, such as the patient's doctor for consultation, and/or be recorded, e.g., in the patient's electronic medical file.

Although illustrative embodiments of the present invention have been described herein, it is to be understood that the invention is not limited to those precise embodiments, and that various other changes and modifications may be made by one skilled in the art without departing from the scope of the invention.

What is claimed is:
1. A device, comprising:
an intake port;
fluidic channels connecting the intake port to detecting chambers, wherein the detecting chambers are configured to permit optical measurements of a fluid sample in the detecting chambers, wherein a size of the fluidic channels differs amongst the fluidic channels to regu- late a flow rate of the fluid sample through the fluidic channels to the detecting chambers, and wherein a length of the fluidic channels between the intake port and the detecting chambers differs amongst the detecting chambers;
- a cover present over and sealing the fluidic channels and the detecting chambers;
- vents leading away from the detecting chambers, wherein the vents are located downstream from the detecting chambers;
- a liquid blocker between the detecting chambers and an opening of the vents, wherein the liquid blocker permits air to pass therethrough while at the same time restricting liquid flow; and
- multiple first waveguides and multiple second waveguides coupled to the detecting chambers, wherein the multiple first waveguides and the multiple second waveguides are in a grid configuration whereby the multiple first waveguides intersect the multiple second waveguides at only a single point along any given one of the fluidic channels.

2. The device of claim 1, further comprising:
mixing chambers fluidly connected to the detecting chambers, wherein the mixing chambers comprise at least one reagent.

3. The device of claim 2, wherein the mixing chambers contain at least two different reagents.

4. The device of claim 2, wherein the mixing chambers contain at least two different amounts of the at least one reagent.

5. The device of claim 1, wherein the fluidic channels comprise at least one delay element having a serpentine configuration.

6. The device of claim 1, wherein the multiple first waveguides are coupled to a first side of the detecting chambers over the cover and the multiple second waveguides are coupled to a second side of the detecting chambers opposite the first side below the substrate, wherein both the cover and the substrate are transparent to light permitting the optical measurements of the fluid sample to be made through the cover and the substrate.

7. The device of claim 1, wherein the multiple first waveguides are connected to multiple light sources and the multiple second waveguides are connected to multiple light detectors, wherein each of the multiple first waveguides and the multiple second waveguides are coupled to more than one of the detecting chambers along different fluidic channels.

8. The device of claim 7, wherein the multiple light sources are configured to produce at least two different wavelengths of light.

9. The device of claim 7, wherein the multiple light detectors are configured to detect at least two different wavelengths of light.

10. A method, comprising:
introducing a fluid sample to a device having an intake port, fluidic channels connecting the intake port to detecting chambers wherein a size of the fluidic channels differs amongst the fluidic channels to regulate a flow rate of the fluid sample through the fluidic channels to the detecting chambers, and wherein a length of the fluidic channels between the intake port and the detecting chambers differs amongst the detecting chambers, a cover present over and sealing the fluidic channels and the detecting chambers, vents leading away from the detecting chambers, wherein the vents are located downstream from the detecting chambers, a liquid blocker between the detecting chambers and an opening of the vents, wherein the liquid blocker permits air to pass therethrough while at the same time restricting liquid flow, and multiple first waveguides and multiple second waveguides coupled to the detecting chambers, wherein the multiple first waveguides and the multiple second waveguides are in a grid configuration whereby the multiple first waveguides intersect the multiple second waveguides at only a single point along any given one of the fluidic channels;
contacting the fluid sample with at least one reagent prior to the fluid sample entering the detecting chambers; and
making optical measurements of the fluid sample in the detecting chambers.

11. The method of claim 10, further comprising:
contacting the fluid sample with different amounts of a given reagent.

12. The method of claim 11, further comprising:
determining a reaction time using a change in optical signal based on when the fluid sample has contacted the given reagent.

13. The method of claim 12, further comprising:
comparing the optical measurements of the fluid sample with reference data taken from samples having a target analyte at known concentrations using the reaction time.

14. The method of claim 10, wherein both the cover and the substrate are transparent to light, and wherein the device further comprises multiple light sources connected to the multiple first waveguides and multiple light detectors connected to the multiple second waveguides, the method further comprising:
generating light using the multiple light sources, wherein the light is carried to the detecting chambers by the multiple first waveguides;
passing the light through the cover, through the fluid sample in the detecting chambers and through the substrate; and
detecting the light that has passed through the fluid sample using the multiple light detectors, wherein the light is carried from the detecting chambers to the multiple light detectors by the multiple second waveguides.

* * * * *